United States Patent
Barnhill et al.

(10) Patent No.: US 7,754,021 B2
(45) Date of Patent: Jul. 13, 2010

(54) WASH CHAMBER FOR APPENDAGE-WASHING APPARATUS

(75) Inventors: Paul R. Barnhill, Aurora, CO (US); Thomas M. Johannsen, Centennial, CO (US)

(73) Assignee: Resurgent Health & Medical, LLC, Golden, CO (US)

( * ) Notice: Subject to any disclaimer, the term of this patent is extended or adjusted under 35 U.S.C. 154(b) by 0 days.

(21) Appl. No.: 12/346,198

(22) Filed: Dec. 30, 2008

(65) Prior Publication Data

US 2009/0107528 A1    Apr. 30, 2009

Related U.S. Application Data

(62) Division of application No. 11/829,781, filed on Jul. 27, 2007, now Pat. No. 7,607,443.

(60) Provisional application No. 60/909,370, filed on Mar. 30, 2007, provisional application No. 60/863,753, filed on Oct. 31, 2006.

(51) Int. Cl.
B08B 3/02 (2006.01)
(52) U.S. Cl. .............................. 134/18; 134/33; 134/34
(58) Field of Classification Search .................. 134/18, 134/32, 33, 34, 42
See application file for complete search history.

(56) References Cited

U.S. PATENT DOCUMENTS

| | | |
|---|---|---|
| 2,325,008 A | 7/1943 | Gruett |
| 2,386,455 A | 10/1945 | Green |
| 2,522,928 A | 9/1950 | Carroll |
| 2,647,801 A | 8/1953 | Lycan |
| 2,769,547 A | 11/1956 | Hirsch |
| 2,826,763 A | 3/1958 | Bass |
| 3,059,815 A | 10/1962 | Parsons, Jr. |
| 3,081,471 A | 3/1963 | Newell |
| 3,220,424 A | 11/1965 | Nelson |
| 3,243,264 A | 3/1966 | Hickey |
| 3,437,274 A | 4/1969 | Apri |
| 3,529,774 A | 9/1970 | Apri |
| 3,639,844 A | 2/1972 | Karklys |

(Continued)

FOREIGN PATENT DOCUMENTS

DE    19903079    8/2000

(Continued)

OTHER PUBLICATIONS

Search Results, Mar. 2007, 27 pages.

(Continued)

*Primary Examiner*—Michael Barr
*Assistant Examiner*—Saeed T Chaudhry
(74) *Attorney, Agent, or Firm*—Sheridan Ross P.C.

(57) ABSTRACT

A wash cylinder or chamber for an automated cleaning station to clean an object or a person's body part includes nozzles on the interior of the cylinder, the nozzles of one embodiment comprising an increasing roll angle providing a novel spray pattern. Additionally, embodiments of the invention include fluid guidance and conveyance structures, angled nozzles, sealing structures, finger guards, nozzle ribs, wash chamber seating mechanisms and drains, and nozzle inlays having a plurality of nozzles. Also disclosed are methods of washing an object or body part using a wash cylinder or chamber and methods of assembling a wash cylinder or chamber.

20 Claims, 24 Drawing Sheets

U.S. PATENT DOCUMENTS

| | | |
|---|---|---|
| 3,647,147 A | 3/1972 | Cook |
| 3,699,984 A | 10/1972 | Davis |
| 3,744,149 A | 7/1973 | Helbling |
| 3,754,559 A | 8/1973 | Seiwert |
| 3,757,806 A * | 9/1973 | Bhaskar et al. .............. 134/191 |
| 3,817,651 A | 6/1974 | Law et al. |
| 3,844,278 A | 10/1974 | Weider |
| 3,881,328 A | 5/1975 | Kleimola et al. |
| 3,918,117 A | 11/1975 | Plante |
| 3,918,987 A | 11/1975 | Kopfer |
| 3,967,478 A | 7/1976 | Guinn |
| 3,992,730 A | 11/1976 | Davis |
| 3,997,873 A | 12/1976 | Thornton |
| 4,001,599 A | 1/1977 | Karklys |
| 4,020,856 A | 5/1977 | Masterson |
| 4,073,301 A | 2/1978 | Mackinnon |
| 4,120,180 A | 10/1978 | Jedora |
| 4,137,929 A | 2/1979 | Grossman |
| 4,219,367 A | 8/1980 | Cary, Jr. et al. |
| 4,275,385 A | 6/1981 | White |
| 4,295,233 A | 10/1981 | Hinkel et al. |
| 4,398,310 A | 8/1983 | Lienhard |
| 4,402,331 A | 9/1983 | Taldo et al. |
| 4,453,286 A | 6/1984 | Wieland |
| 4,496,519 A | 1/1985 | McGuire |
| 4,509,543 A | 4/1985 | Livingston et al. |
| 4,601,064 A | 7/1986 | Shipley |
| 4,606,085 A | 8/1986 | Davies |
| 4,606,500 A | 8/1986 | Mussler et al. |
| 4,670,010 A | 6/1987 | Dragone |
| 4,688,585 A | 8/1987 | Vetter |
| 4,769,863 A | 9/1988 | Tegg et al. |
| 4,817,651 A | 4/1989 | Crisp et al. |
| 4,896,144 A | 1/1990 | Bogstad |
| 4,916,435 A | 4/1990 | Fuller |
| 4,921,211 A | 5/1990 | Novak et al. |
| 4,925,495 A | 5/1990 | Crisp et al. |
| 4,942,631 A | 7/1990 | Rosa |
| 4,999,613 A | 3/1991 | Williamson et al. |
| 5,016,172 A | 5/1991 | Dessertine |
| 5,031,258 A | 7/1991 | Shaw |
| 5,060,323 A | 10/1991 | Shaw |
| 5,074,322 A | 12/1991 | Jaw |
| RE33,810 E | 2/1992 | Strieter |
| 5,086,526 A | 2/1992 | Van Marcke |
| 5,119,104 A | 6/1992 | Heller |
| 5,184,642 A | 2/1993 | Powell |
| 5,193,563 A | 3/1993 | Melech |
| 5,199,118 A | 4/1993 | Cole et al. |
| 5,202,666 A | 4/1993 | Knippscheer |
| 5,238,749 A | 8/1993 | Cueman et al. |
| 5,257,423 A | 11/1993 | Jacobsen et al. |
| 5,265,628 A | 11/1993 | Sage et al. |
| 5,291,399 A | 3/1994 | Chaco |
| 5,340,581 A | 8/1994 | Tseng et al. |
| 5,387,993 A | 2/1995 | Heller et al. |
| RE35,035 E | 9/1995 | Shipley |
| 5,455,851 A | 10/1995 | Chaco et al. |
| 5,465,082 A | 11/1995 | Chaco |
| 5,503,840 A | 4/1996 | Jacobson et al. |
| 5,515,426 A | 5/1996 | Yacenda et al. |
| 5,548,637 A | 8/1996 | Heller et al. |
| 5,561,412 A | 10/1996 | Novak et al. |
| 5,572,195 A | 11/1996 | Heller et al. |
| 5,594,786 A | 1/1997 | Chaco et al. |
| 5,601,100 A | 2/1997 | Kawakami et al. |
| 5,610,589 A | 3/1997 | Evans et al. |
| 5,633,742 A | 5/1997 | Shipley |
| 5,670,945 A | 9/1997 | Applonie |
| 5,689,229 A | 11/1997 | Chaco et al. |
| 5,695,091 A | 12/1997 | Winings et al. |
| 5,699,038 A | 12/1997 | Ulrich et al. |
| 5,702,115 A | 12/1997 | Pool |
| 5,727,579 A | 3/1998 | Chardack |
| 5,745,272 A | 4/1998 | Shipley |
| 5,765,242 A | 6/1998 | Marciano |
| 5,774,865 A | 6/1998 | Glynn |
| 5,781,942 A | 7/1998 | Allen et al. |
| 5,793,653 A | 8/1998 | Segal |
| 5,808,553 A | 9/1998 | Cunningham |
| 5,812,059 A | 9/1998 | Shaw et al. |
| 5,818,617 A | 10/1998 | Shipley |
| 5,822,418 A | 10/1998 | Yacenda et al. |
| 5,822,544 A | 10/1998 | Chaco et al. |
| 5,823,447 A * | 10/1998 | Maybach .................... 239/596 |
| 5,838,223 A | 11/1998 | Gallant et al. |
| 5,845,225 A | 12/1998 | Mosher |
| 5,860,437 A | 1/1999 | Fernie |
| 5,863,497 A | 1/1999 | Dirksing |
| 5,870,015 A | 2/1999 | Hinkel |
| 5,900,067 A | 5/1999 | Jones |
| 5,900,801 A | 5/1999 | Heagle et al. |
| 5,924,148 A | 7/1999 | Flowers, Sr. |
| 5,939,974 A | 8/1999 | Heagle et al. |
| 5,945,068 A | 8/1999 | Ferone |
| 5,945,910 A | 8/1999 | Gorra |
| 5,952,924 A | 9/1999 | Evans et al. |
| 5,954,069 A | 9/1999 | Foster |
| 5,966,573 A | 10/1999 | Yu et al. |
| 5,966,753 A | 10/1999 | Gauthier et al. |
| 5,972,126 A | 10/1999 | Fernie |
| 5,979,500 A | 11/1999 | Jahrling et al. |
| 5,992,430 A | 11/1999 | Chardack et al. |
| 6,029,600 A | 2/2000 | Davis |
| 6,031,461 A | 2/2000 | Lynn |
| 6,037,871 A | 3/2000 | Babylon |
| 6,038,331 A | 3/2000 | Johnson |
| 6,038,519 A | 3/2000 | Gauthier et al. |
| 6,110,292 A | 8/2000 | Jewett et al. |
| 6,125,482 A | 10/2000 | Foster |
| 6,131,587 A | 10/2000 | Chardack et al. |
| 6,147,607 A | 11/2000 | Lynn |
| 6,161,227 A | 12/2000 | Bargenquast |
| 6,176,941 B1 | 1/2001 | Jewett et al. |
| 6,195,588 B1 | 2/2001 | Gauthier et al. |
| 6,211,788 B1 | 4/2001 | Lynn et al. |
| 6,232,870 B1 | 5/2001 | Garber et al. |
| 6,235,351 B1 | 5/2001 | DiMarzio et al. |
| 6,236,317 B1 | 5/2001 | Cohen et al. |
| 6,236,953 B1 | 5/2001 | Segal |
| 6,268,797 B1 | 7/2001 | Berube et al. |
| 6,278,372 B1 | 8/2001 | Velasco, Jr. et al. |
| 6,317,717 B1 | 11/2001 | Lindsey et al. |
| 6,335,686 B1 | 1/2002 | Goff et al. |
| 6,344,794 B1 | 2/2002 | Ulrich et al. |
| 6,351,866 B1 | 3/2002 | Bragulla |
| 6,392,546 B1 | 5/2002 | Smith |
| 6,399,853 B1 | 6/2002 | Roe et al. |
| 6,404,837 B1 | 6/2002 | Thompson et al. |
| 6,413,921 B1 | 7/2002 | Childers et al. |
| 6,417,773 B1 | 7/2002 | Vlahos et al. |
| 6,424,262 B2 | 7/2002 | Garber et al. |
| 6,426,701 B1 | 7/2002 | Levy et al. |
| 6,431,189 B1 | 8/2002 | Deibert |
| 6,448,886 B2 | 9/2002 | Garber et al. |
| 6,462,656 B2 | 10/2002 | Ulrich et al. |
| 6,486,780 B1 | 11/2002 | Garber et al. |
| 6,523,193 B2 | 2/2003 | Saraya |
| 6,524,390 B1 | 2/2003 | Jones |
| 6,539,393 B1 | 3/2003 | Kabala |
| 6,542,568 B1 | 4/2003 | Howes, Jr. et al. |
| 6,577,240 B2 | 6/2003 | Armstrong |
| 6,600,420 B2 | 7/2003 | Goff et al. |
| 6,663,719 B2 | 12/2003 | Shinozaki et al. |

| | | |
|---|---|---|
| 6,671,890 B2 | 1/2004 | Nishioka |
| 6,706,243 B1 | 3/2004 | Sias et al. |
| 6,707,873 B2 | 3/2004 | Thompson et al. |
| 6,727,818 B1 | 4/2004 | Wildman et al. |
| 6,733,595 B1 | 5/2004 | Grillo |
| 6,759,959 B2 | 7/2004 | Wildman |
| 6,768,419 B2 | 7/2004 | Garber et al. |
| 6,825,763 B2 | 11/2004 | Ulrich et al. |
| 6,832,916 B2 | 12/2004 | Collopy |
| 6,882,278 B2 | 4/2005 | Winings et al. |
| 6,883,563 B2 | 4/2005 | Smith |
| 6,892,143 B2 | 5/2005 | Howes, Jr. et al. |
| 6,902,397 B2 | 6/2005 | Farrell et al. |
| 6,938,282 B2 | 9/2005 | Yamamoto |
| 6,956,498 B1 | 10/2005 | Gauthier et al. |
| 6,970,574 B1 | 11/2005 | Johnson |
| D512,648 S | 12/2005 | Smith et al. |
| 6,975,231 B2 | 12/2005 | Lane et al. |
| 6,992,561 B2 | 1/2006 | Sandt et al. |
| 7,010,369 B2 | 3/2006 | Borders et al. |
| 7,015,816 B2 | 3/2006 | Wildman et al. |
| 7,020,508 B2 | 3/2006 | Stivoric et al. |
| 7,080,061 B2 | 7/2006 | Kabala |
| 7,107,631 B2 | 9/2006 | Lang et al. |
| 7,113,094 B2 | 9/2006 | Garber et al. |
| 7,119,688 B2 | 10/2006 | Wildman |
| 7,120,800 B2 | 10/2006 | Ginter et al. |
| 7,123,151 B2 | 10/2006 | Garber et al. |
| 7,150,293 B2 | 12/2006 | Jonte |
| 7,174,577 B2 | 2/2007 | Jost et al. |
| 7,242,306 B2 | 7/2007 | Wildman et al. |
| 7,242,307 B1 | 7/2007 | LeBlond et al. |
| 7,248,933 B2 | 7/2007 | Wildman |
| 7,270,268 B2 | 9/2007 | Garber et al. |
| 7,271,719 B2 | 9/2007 | Ku et al. |
| 7,271,728 B2 | 9/2007 | Taylor et al. |
| 7,423,533 B1 | 9/2008 | LeBlond et al. |
| 7,443,305 B2 | 10/2008 | Verdiramo |
| 2002/0019709 A1 | 2/2002 | Segal |
| 2002/0104083 A1 | 8/2002 | Hendricks et al. |
| 2002/0135486 A1 | 9/2002 | Brohagen et al. |
| 2002/0175182 A1 | 11/2002 | Matthews |
| 2003/0069815 A1 | 4/2003 | Eisenberg et al. |
| 2003/0089771 A1 | 5/2003 | Cybulski et al. |
| 2003/0197122 A1 | 10/2003 | Faiola et al. |
| 2004/0083547 A1 | 5/2004 | Mercier |
| 2004/0133081 A1 | 7/2004 | Teller et al. |
| 2004/0150527 A1 | 8/2004 | Harper et al. |
| 2004/0255409 A1 | 12/2004 | Hilscher et al. |
| 2005/0134465 A1 | 6/2005 | Rice et al. |
| 2005/0136949 A1 | 6/2005 | Barnes |
| 2005/0139239 A1 | 6/2005 | Prae |
| 2005/0147526 A1 | 7/2005 | Hishida |
| 2005/0151641 A1 | 7/2005 | Ulrich et al. |
| 2005/0171634 A1 | 8/2005 | York et al. |
| 2005/0248461 A1 | 11/2005 | Lane et al. |
| 2006/0122474 A1 | 6/2006 | Teller et al. |
| 2006/0132316 A1 | 6/2006 | Wildman et al. |
| 2006/0224051 A1 | 10/2006 | Teller et al. |
| 2006/0229891 A1 | 10/2006 | Grier |
| 2006/0231568 A1 | 10/2006 | Lynn et al. |
| 2006/0241396 A1 | 10/2006 | Fabian et al. |
| 2006/0264730 A1 | 11/2006 | Stivoric et al. |
| 2007/0011893 A1 | 1/2007 | Garber et al. |
| 2007/0020212 A1 | 1/2007 | Bernalet et al. |
| 2007/0247316 A1 | 10/2007 | Wildman et al. |
| 2007/0257803 A1 | 11/2007 | Munro et al. |
| 2007/0273525 A1 | 11/2007 | Garber et al. |
| 2008/0001763 A1 | 1/2008 | Raja et al. |
| 2008/0031838 A1 | 2/2008 | Bolling |
| 2008/0099043 A1 | 5/2008 | Barnhill et al. |
| 2008/0099045 A1 | 5/2008 | Glenn et al. |
| 2008/0099046 A1 | 5/2008 | Barnhill et al. |
| 2008/0099047 A1 | 5/2008 | Barnhill et al. |
| 2008/0099048 A1 | 5/2008 | Barnhill et al. |
| 2008/0099049 A1 | 5/2008 | Barnhill et al. |
| 2008/0099050 A1 | 5/2008 | Barnhill |
| 2008/0100441 A1 | 5/2008 | Prodanovich et al. |
| 2008/0103636 A1 | 5/2008 | Glenn et al. |
| 2009/0083970 A1 | 4/2009 | Barnhill et al. |
| 2009/0084407 A1 | 4/2009 | Glenn et al. |
| 2009/0084414 A1 | 4/2009 | Barnhill et al. |
| 2009/0084417 A1 | 4/2009 | Barnhill et al. |
| 2009/0090389 A1 | 4/2009 | Barnhill et al. |
| 2009/0090390 A1 | 4/2009 | Barnhill et al. |
| 2009/0094814 A1 | 4/2009 | Barnhill et al. |

FOREIGN PATENT DOCUMENTS

| | | |
|---|---|---|
| EP | 0396039 | 11/1990 |
| EP | 0616658 | 9/1994 |
| EP | 0758702 | 2/1997 |
| EP | 1872802 | 1/2008 |
| EP | 1935515 | 6/2008 |
| FR | 2659217 | 9/1991 |
| GB | 2324397 | 10/1998 |
| JP | 5-329065 | 12/1993 |
| WO | WO 80/01983 | 10/1980 |
| WO | WO 93/10311 | 5/1993 |
| WO | WO 03/086274 | 10/2003 |

OTHER PUBLICATIONS

Background section of the above-captioned application (previously provided).
International Preliminary Report on Patentability for International (PCT) Patent Application No. PCT/US07/749950, mailed May 14, 2009.
Official Action for U.S. Appl. No. 11/829,764, mailed Jan. 6, 2009.
Official Action for U.S. Appl. No. 11/829,769, mailed Feb. 11, 2009.
Official Action for U.S. Appl. No. 11/829,775, mailed Jan. 6, 2009.
Notice of Allowance for U.S. Appl. No. 11/829,775, mailed Jun. 15, 2009.
Official Action for U.S. Appl. No. 11/829,781, mailed Jan. 6, 2009.
Notice of Allowance for U.S. Appl. No. 11/829,781, mailed Jun. 15, 2009.
Official Action for U.S. Appl. No. 11/829,783, mailed Jan. 8, 2009.
Official Action for U.S. Appl. No. 11/829,783, mailed Jun. 24, 2009.
"Case Study: FL hospital used IT to monitor hand washing", FierceHealthIT website, dated Aug. 3, 2009, available at http://www.fiercehealthit.com/node/8503/print, printed on Aug. 11, 2009, p. 1.
U.S. Appl. No. 12/432,693, filed Apr. 29, 2009, Barnhill.
U.S. Appl. No. 12/432,698, filed Apr. 29, 2009, Barnhill et al.
U.S. Appl. No. 12/432,711, filed Apr. 29, 2009, Glenn, et al.
U.S. Appl. No. 12/432,716, filed Apr. 29, 2009, Barnhill.
U.S. Appl. No. 12/432,718, filed Apr. 29, 2009, Barnhill, et al.
"Michigan IT Companies Helping the University of Miami Center for Patient Safety Tackle a Leading Cause of Death Using an RTLS Solution to Monitor Staff Hand-Washing Compliance", prnewswire website, dated Jul. 29, 2009, available at http://news.prnewswire.com/DisplayReleaseContent.aspx?ACCT=104&STORY=/www/story/07-29-2009/0005068398&EDATE, printed on Aug. 10, 2009, pp. 1-2.
"HYGREEN The Intelligent Hand Hygiene Solution", Xhale, Inc., date unknown, 2 pages.
"HyGreen: How it Works", available at http://www.xhale.com/hygreen/solution/How.asp, printed Jul. 14, 2009, pp. 1-2.
"HyGreen: Sample Reporting", available at http://www.xhale.com/hygreen/solution/Reporting.asp, printed Jul. 14, 2009, pp. 1-3.
Notice of Allowance for U.S. Appl. No. 11/829,764, mailed Jul. 2, 2009.
Notice of Allowance for U.S. Appl. No. 11/829,769, mailed Aug. 31, 2009.
Official Action for U.S. Appl. No. 12/331,118, mailed Oct. 1, 2009.
Official Action for U.S. Appl. No. 12/330,145, mailed Oct. 1, 2009.
Official Action for U.S. Appl. No. 11/829,783, mailed Oct. 9, 2009.

"HandGiene" available at http://handgienecorp.com/index.jsp, printed Nov. 2, 2009, pp. 1-2.

International Search Report for International (PCT) Patent Application No. PCT/US07/749950, mailed Aug. 27, 2008.

Written Opinion for International (PCT) Patent Application No. PCT/US07/749950, mailed Aug. 27, 2008.

Official Action for U.S. Appl. No. 12/331,175, mailed Dec. 16, 2009.

Official Action for U.S. Appl. No. 12/331,038, mailed Dec. 11, 2009.

Official Action for U.S. Appl. No. 12/330,179, mailed Dec. 16, 2009.

* cited by examiner

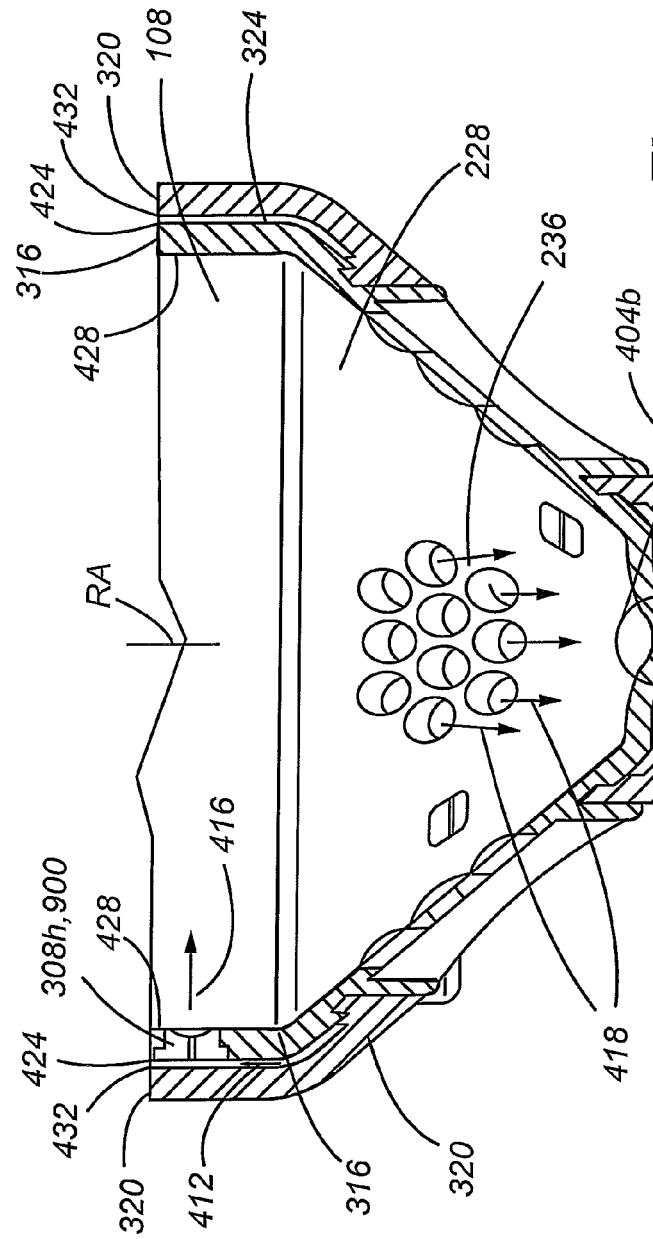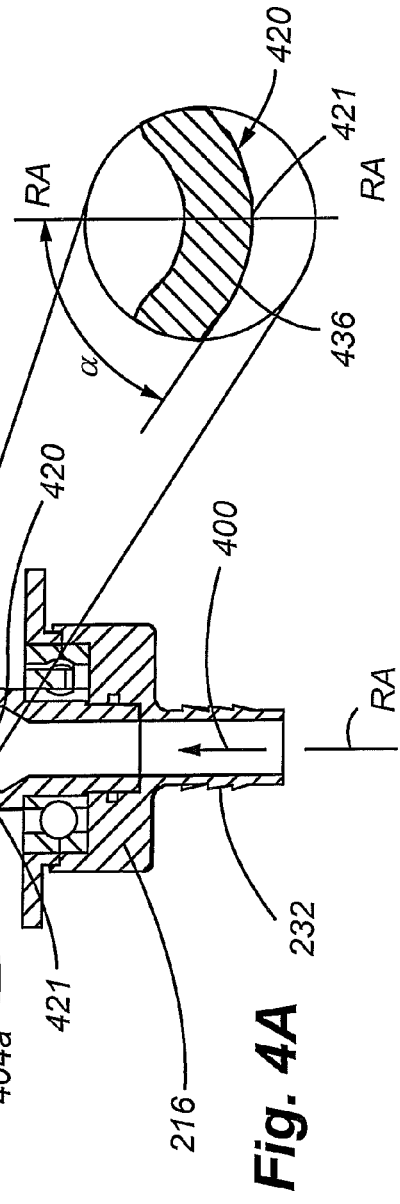
Fig. 4A
Fig. 4B

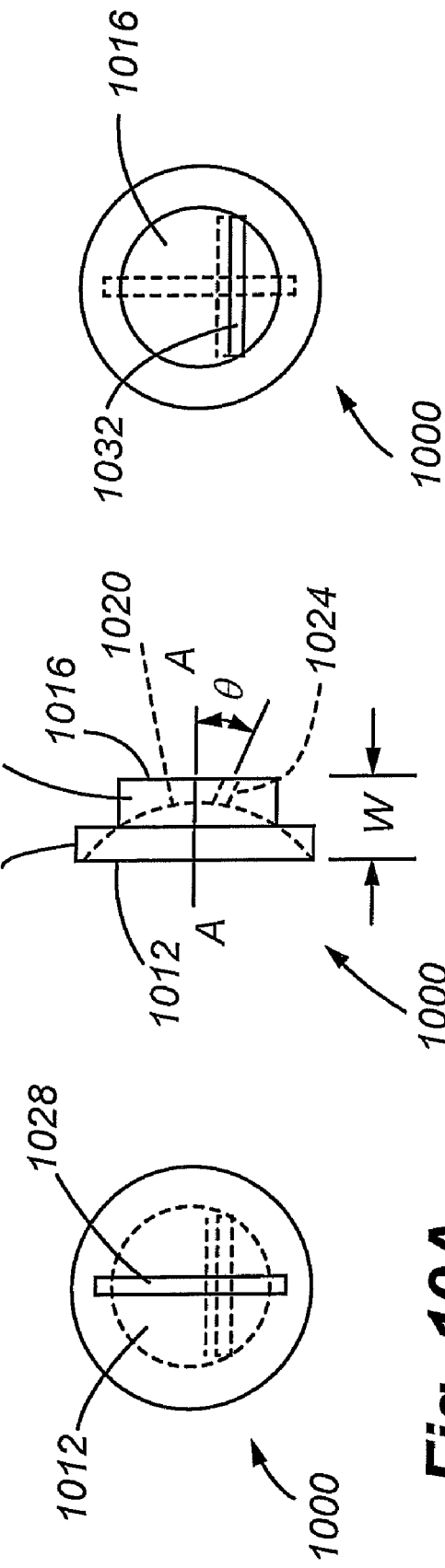

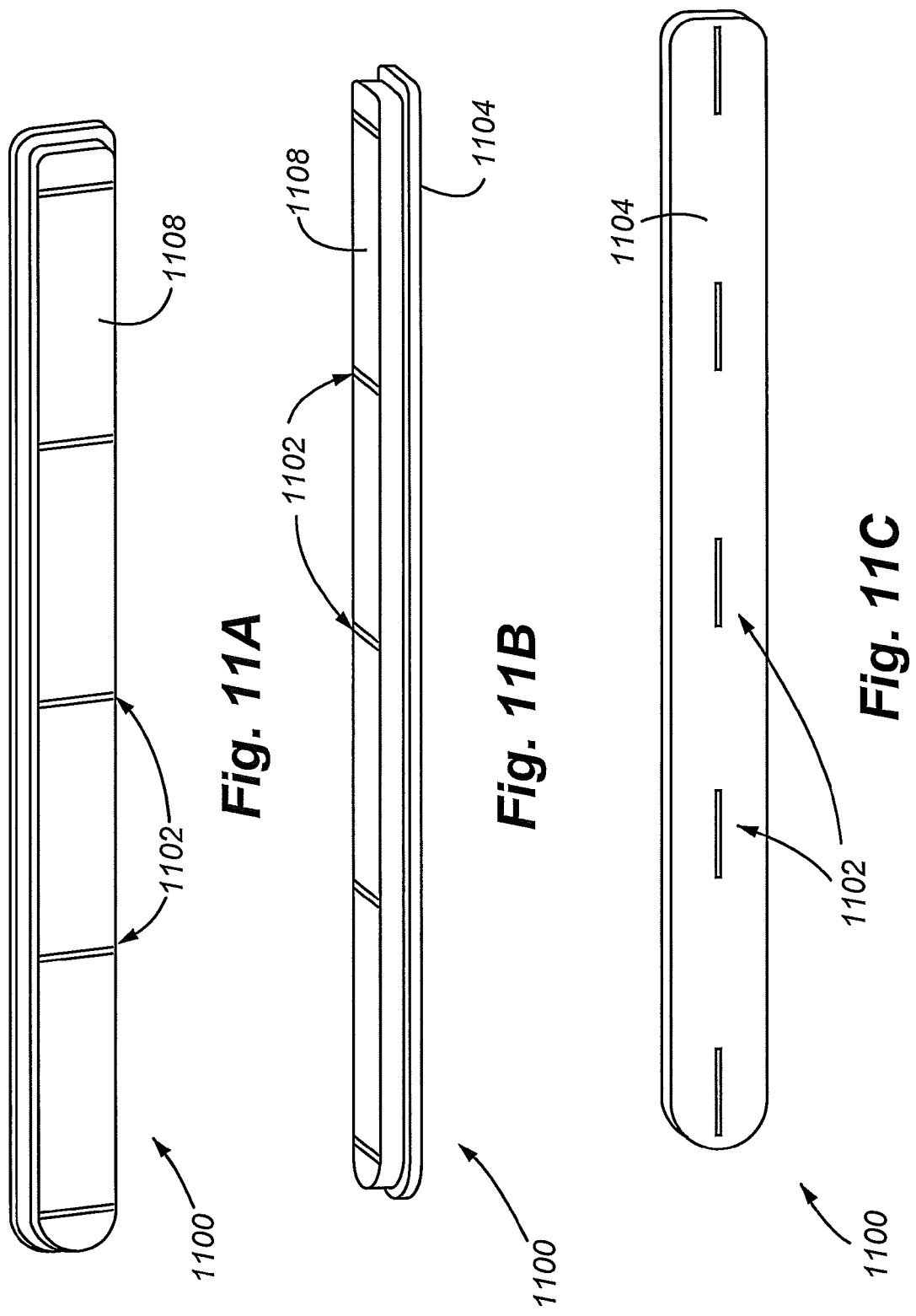

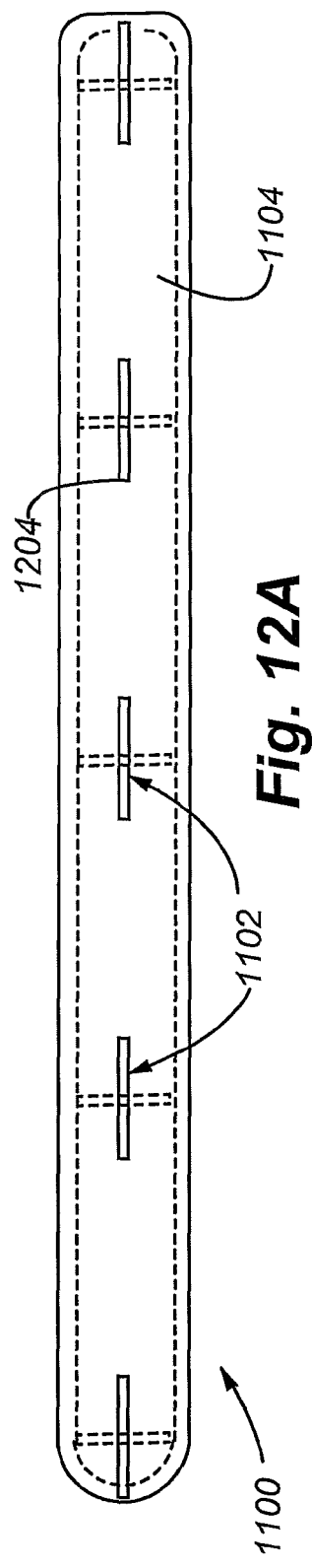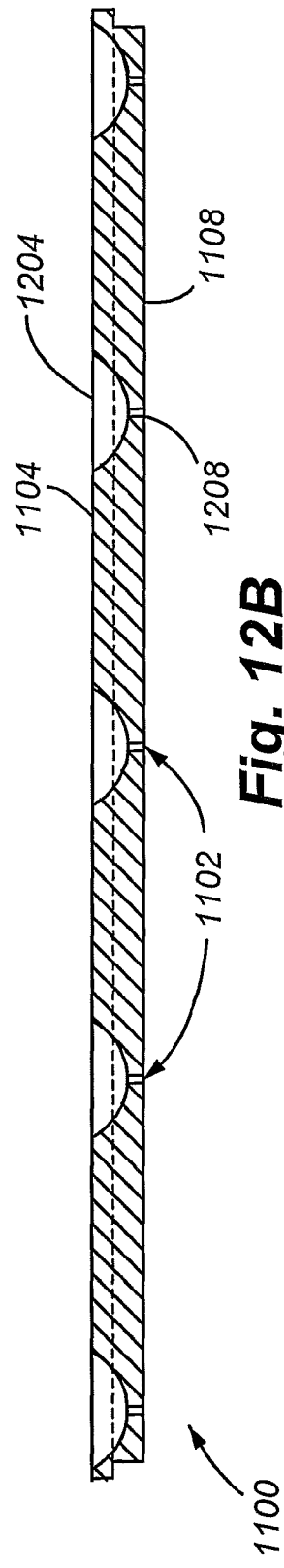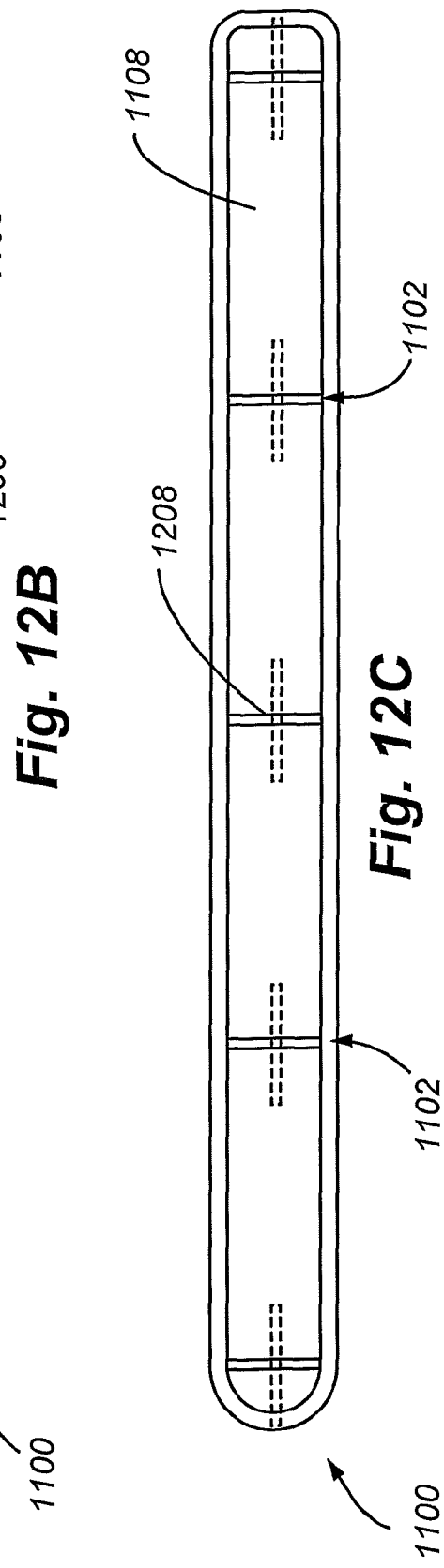

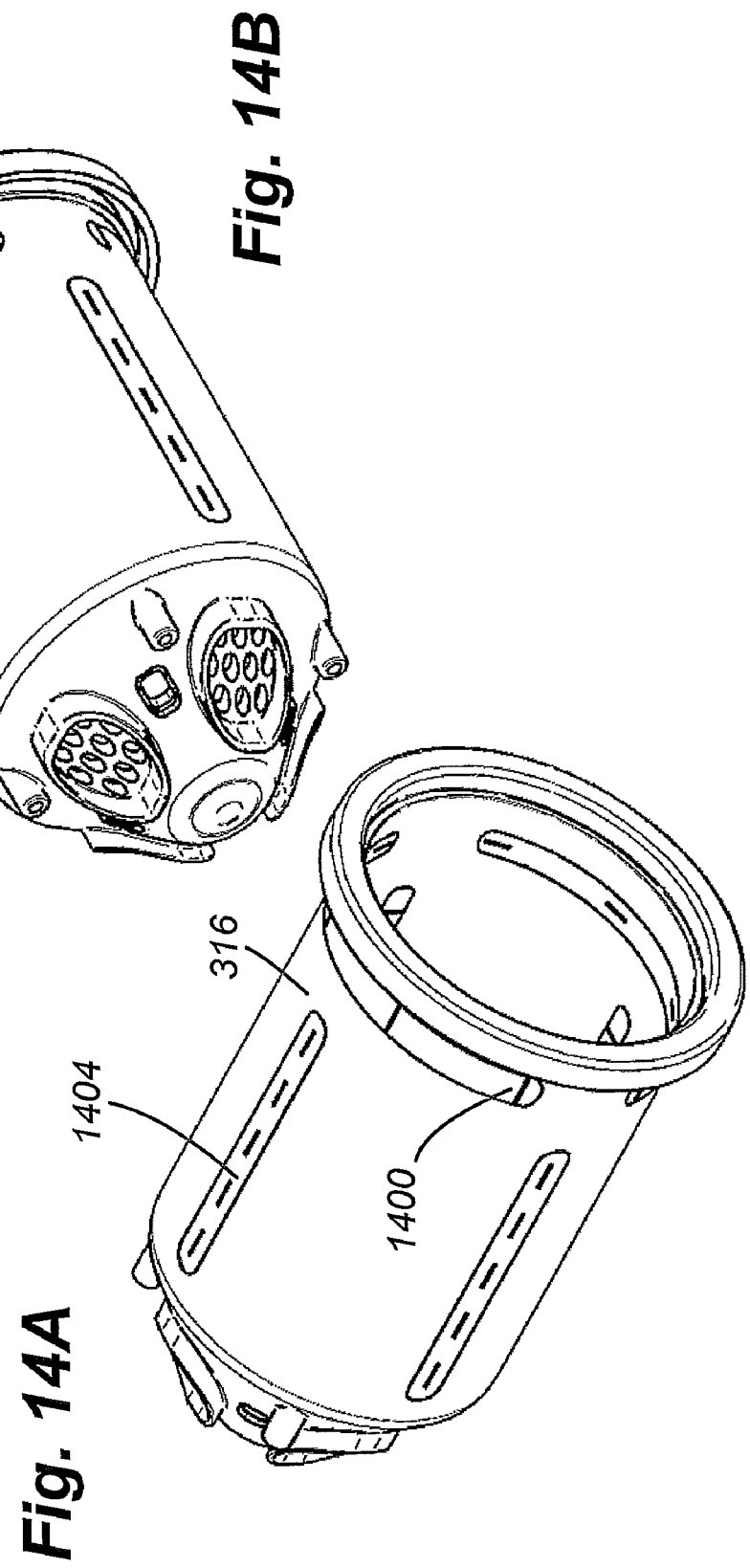

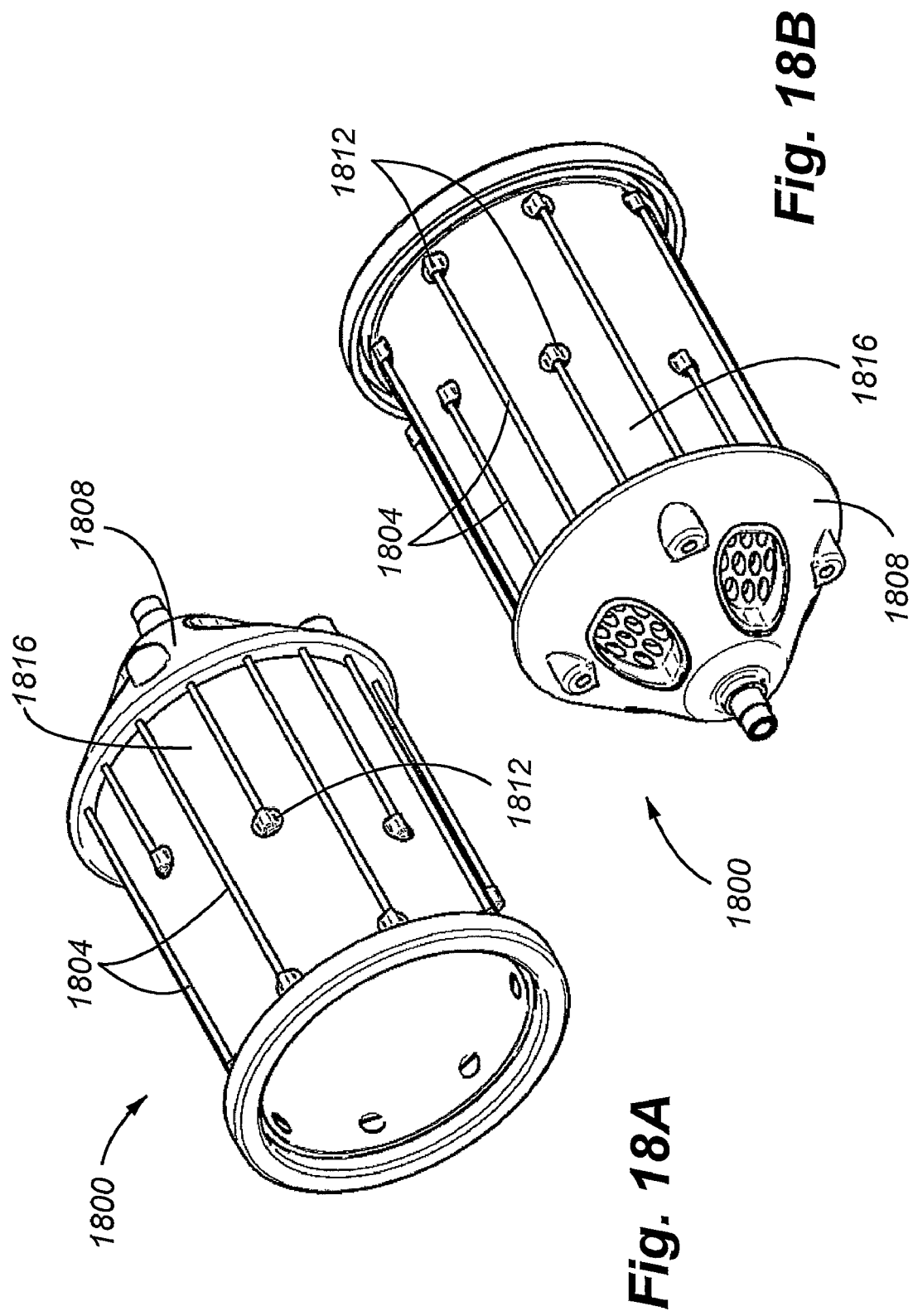

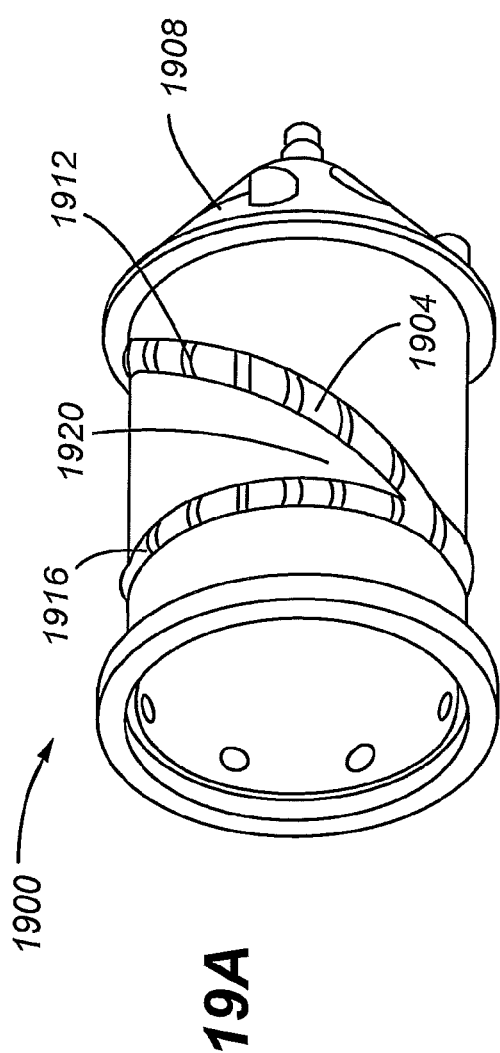
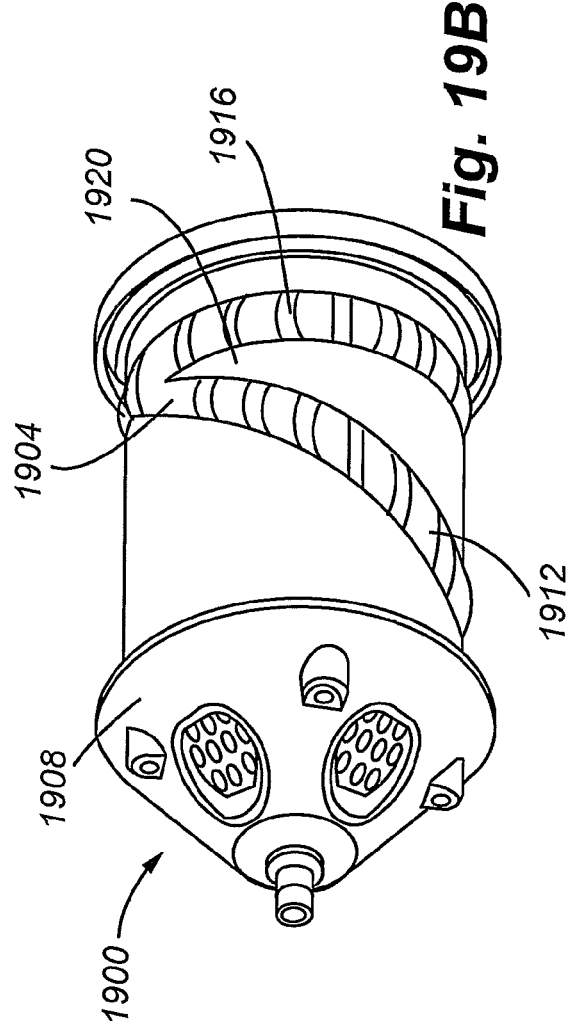

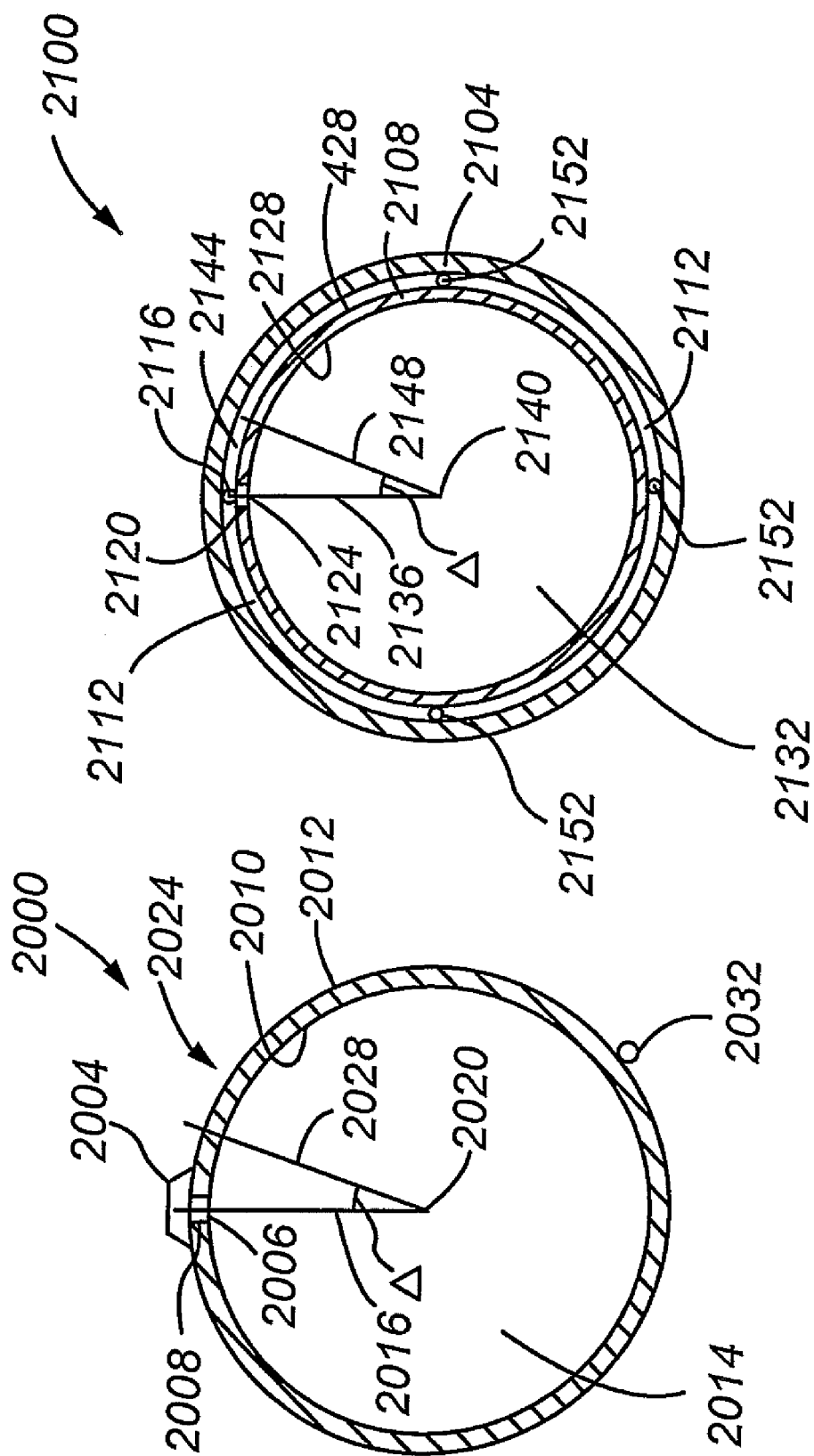

WASH CHAMBER FOR APPENDAGE-WASHING APPARATUS

CROSS-REFERENCE TO RELATED APPLICATIONS

The present application is a divisional of U.S. patent application Ser. No. 11/829,781, filed Jul. 27, 2007, entitled "Wash Chamber for Automated Appendage-Washing Apparatus" which claims the benefit of U.S. Provisional Patent Application Ser. No. 60/863,753 filed on Oct. 31, 2006, and U.S. Provisional Patent Application Ser. No. 60/909,370, filed on Mar. 30, 2007, the entire contents of which are incorporated herein by reference in their entirety. In addition, the present application cross-references, but does not claim priority to U.S. patent application Ser. No. 11/689,582 filed Mar. 22, 2007, the entire content of which are incorporated herein by reference in its entirety for at least the purposes of enablement and written description.

FIELD

The present invention relates to wash chambers for use in automated cleaning systems, and more particularly, to wash chambers used in automated washing devices used to clean at least a portion of an object or an appendage of a user.

BACKGROUND

The following text should not be construed as an admission of knowledge in the prior art. Furthermore, citation or identification of any document in this application is not an admission that such document is available as prior art to the present invention, or that any reference forms a part of the common general knowledge in the art.

Touchless automated hand-washing devices that incorporate rotating cylinders are known and have been in use for some time. These devices are designed to wash and/or provide a proper amount of anti-microbial solution to a person's hand and forearm within in a set time. The cylinders can be mounted in a free standing device and are adapted to receive the person's hand and forearm. The cylinders include an annulus or inner cavity that, in operation, is filled with cleaning fluid. As the inner cavity is filled, the cleaning fluid is forced out of a nozzle arrangement on the inner surface of the cylinder and into the interior of the cylinder. In order to provide greater coverage of the hand and forearm, the cylinders are rotated to provide a spray pattern.

A nozzle arrangement known in the prior art is disclosed by U.S. Pat. No. 4,817,651 ("the '651 patent"). This patent discloses a three-set grouping of nozzles positioned on the interior surface of the rotating cylinder. A first set of nozzles is positioned on a closed end of the cylinder opposite from an open end through which a person's hands are placed. The closed end includes a frusto-conical shape that allows the first set of nozzles to be positioned such that cleaning fluid is sprayed toward the user's hand. Additionally, the frusto-conical end portion may include a drain through which spent cleaning fluid may exit the cylinder. A second set of nozzles are arranged in a ring on the inner surface of the cylinder just inside the open end. The second set of nozzles are angled downward, such that their spray is directed into the cylinder. A third set of nozzles are positioned in a helical array along the length of the cylinder.

As described in the '651 patent, the three-set nozzle arrangement has several advantages. Firstly, the fingernails and the ends of the fingers receive a direct spray from the first set of nozzles. Secondly, the spray pattern that results from the second set of nozzles produces a "curtain" that prevents the cleaning fluid from being splashed or sprayed out of the cylinder. Lastly, the helical arrangement of nozzles along the length of the cylinder in combination the rotation of the cylinders results in debris and spent cleaning fluid being swept downward, toward the closed end of the cylinder. In particular, the third set of nozzles are disposed in a left-hand helical pattern which, when combined with the clock-wise rotation of the cylinders, results in a succession of sprays that travel down the arm from above the wrist towards the fingertips.

The spray pattern that results from the nozzle arrangement depends in part on the orientation and spray pattern of the individual nozzles. While the '651 patent contains little discussion of these details, U.S. Pat. No. 5,823,447 ("the '447 patent") is directed to an angled fan nozzle for use with a rotating cleaning cylinder. The nozzle construction disclosed in the '447 patent produces a flat "fan" pattern. In particular, cleaning fluid is ejected into the interior of the cylinder from a nozzle having a small square aperture. The spray of cleaning fluid spreads out through an angle while remaining substantially in a single plane. The nozzle is constructed such that the plane of the fan spray pattern is angled at 15 degrees with respect to the axis of the nozzle. As described by in the '447 patent, the nozzle may be positioned on the interior of the cylinder at a 15 degree tilt towards the closed end of the cylinder. The 15 degree angle of the fan spray combines with the 15 degrees tilt of the nozzle, resulting in a fan spray directed partially downwards, towards the closed end of the cylinder. With respect to the plane of the cylinder opening, the fan spray is directed downward at a 30 degree angle. This downwardly angled fan spray operates to direct spent cleaning fluid downwards, towards the closed end of the cylinder.

While the '447 patent discloses an angle of the flat fan spray with respect to the plane of the cylinder opening, this reference is silent as to the rotational orientation of the fan spray pattern around with respect to the normal of the inner wall (or "roll" angle as defined later herein). For example, a particular nozzle may be positioned in a 0 degree rotational orientation, such that the flat fan spray is ejected from the nozzle "horizontally," that is, in a plane parallel with the plane of the cylinder opening. Alternatively, a particular nozzle may be positioned in the 90 degree orientation such that the flat fan spray is ejected "vertically," that is, in a plane perpendicular to the plane of the cylinder opening. As can be appreciated, a particular nozzle can be positioned at any angle between 0 and 90 degrees such that the flat fan spray has both a vertical and horizontal component.

It has been found that particular orientations and arrangements of nozzles not disclosed or suggested by the '651 patent or the '447 patent, such as the rotational orientation of particular nozzles, produce a novel spray pattern having increased coverage of the hand and forearm of the user. Additionally, the prior art fails to disclose other novel features associated with the cylinders that allow for faster and more reliable completion of wash cycles, safer operation, and easier assembly.

Nothing herein is to be construed as an admission that the present invention is not entitled to antedate a patent, publication or invention by another by virtue of prior invention.

SUMMARY

It is to be understood that the present invention includes a variety of different versions or embodiments, and this Summary is not meant to be limiting or all-inclusive. This Summary provides some general descriptions of some of the embodiments, but may also include some more specific descriptions of certain embodiments.

The present invention is directed to a chamber, such as a wash chamber or cylinder, for use in connection with an automated fluid dispensing apparatus, such as a hand-washing machine. An embodiment of the wash cylinder described herein includes a plurality of nozzles disposed on the interior of the cylinder that deliver water and/or cleaning fluid as the cylinder rotates around a person's hand and forearm. The cylinder includes an inner cylinder coupled to an outer cylinder. Water and/or cleaning fluid is delivered to the nozzles through an inner cavity located between the inner and outer cylinders.

Wash cylinders in accordance with embodiments of the present invention include features that allow for fast, reliable delivery of water and/or cleaning fluid. At least one embodiment of the present invention comprises a cylinder that includes a flow guidance structure disposed on a surface of the inner cylinder that reduces turbulence of the incoming fluid flow. Additionally, the cylinder may include a sealing mechanism that results in greater reliability under high pressure conditions.

Cylinders in accordance with embodiments of the present invention include drain holes sized to prevent fingers and/or jewelry from being caught while the cylinder is in motion. In particular, the drain holes or perforations are preferably between in 1/32 inch to 1/4 inch in diameter. Additionally, embodiments of the cylinder include structure that prevents fingers and/or jewelry from being caught between the rotating cylinder and non-moving parts of the machine.

Cylinders in accordance with embodiments of the present invention include features that produce an advantageous spray pattern. Like the prior art, at least one embodiment of the present invention uses a three-set nozzle arrangement having a bottom nozzle set, a top ring nozzle set, and a helical array nozzle set. In contrast to the prior art, the present invention includes a novel arrangement of helical nozzles that produce improved coverage of the hand and forearm of the user. In particular, a helical array of nozzles having progressively steeper rotational angles is disclosed. Additionally, embodiments of the present invention include one or more off-helix nozzles.

Embodiments of the present invention may comprise a nozzle strip or inlay that includes a plurality of nozzles along a preferred alignment, such as a linear alignment, a helical alignment, and/or a curved alignment.

Embodiments of the presents may comprise a fluid conveyance feature to limit fluid volumes and decrease the cycle time.

Embodiments of the present invention may comprise any one or more of the novel features described herein, including the in the Detailed Description, and/or shown in the drawings.

As used herein, "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

Various embodiments of the present invention are set forth in the attached figures and in the detailed description of the invention as provided herein and as embodied by the claims. It should be understood, however, that this Summary does not contain all of the aspects and embodiments of the present invention, is not meant to be limiting or restrictive in any manner, and that the invention as disclosed herein is and will be understood by those of ordinary skill in the art to encompass obvious improvements and modifications thereto.

Additional advantages of the present invention will become readily apparent from the following discussion, particularly when taken together with the accompanying drawings.

BRIEF DESCRIPTION OF THE DRAWINGS

FIG. 4A is a cross-sectional view of the closed end of the wash cylinder and the seating assembly shown in FIG. 2A;

FIG. 4B is a detail view of a portion of FIG. 4A;

FIG. 10A is an elevation view of the inlet side of an angled nozzle;

FIG. 10B is a side elevation view of an angled nozzle;

FIG. 10C is an elevation view of outlet side of an angled nozzle;

FIGS. 11A-C are perspective views of a nozzle inlay;

FIG. 12A is an elevation view of the inlet side of a nozzle inlay;

FIG. 12B is a cross-sectional view of a nozzle inlay;

FIG. 12C is an elevation view of the outlet side of a nozzle inlay;

FIGS. 14A-B are perspective views of an inner cylinder having a nozzle inlay;

FIGS. 18A-B are a perspective views of another embodiment of the present invention having a fluid conveyance structure;

FIGS. 19A-B are perspective views of yet another embodiment of the present invention having a fluid conveyance structure;

FIG. 20 is a cross-sectional view of cylinder in accordance with an embodiment of the present invention; and FIG. 21 is a cross-sectional view of wash chamber in accordance with an embodiment of the present invention.

Figure 1:
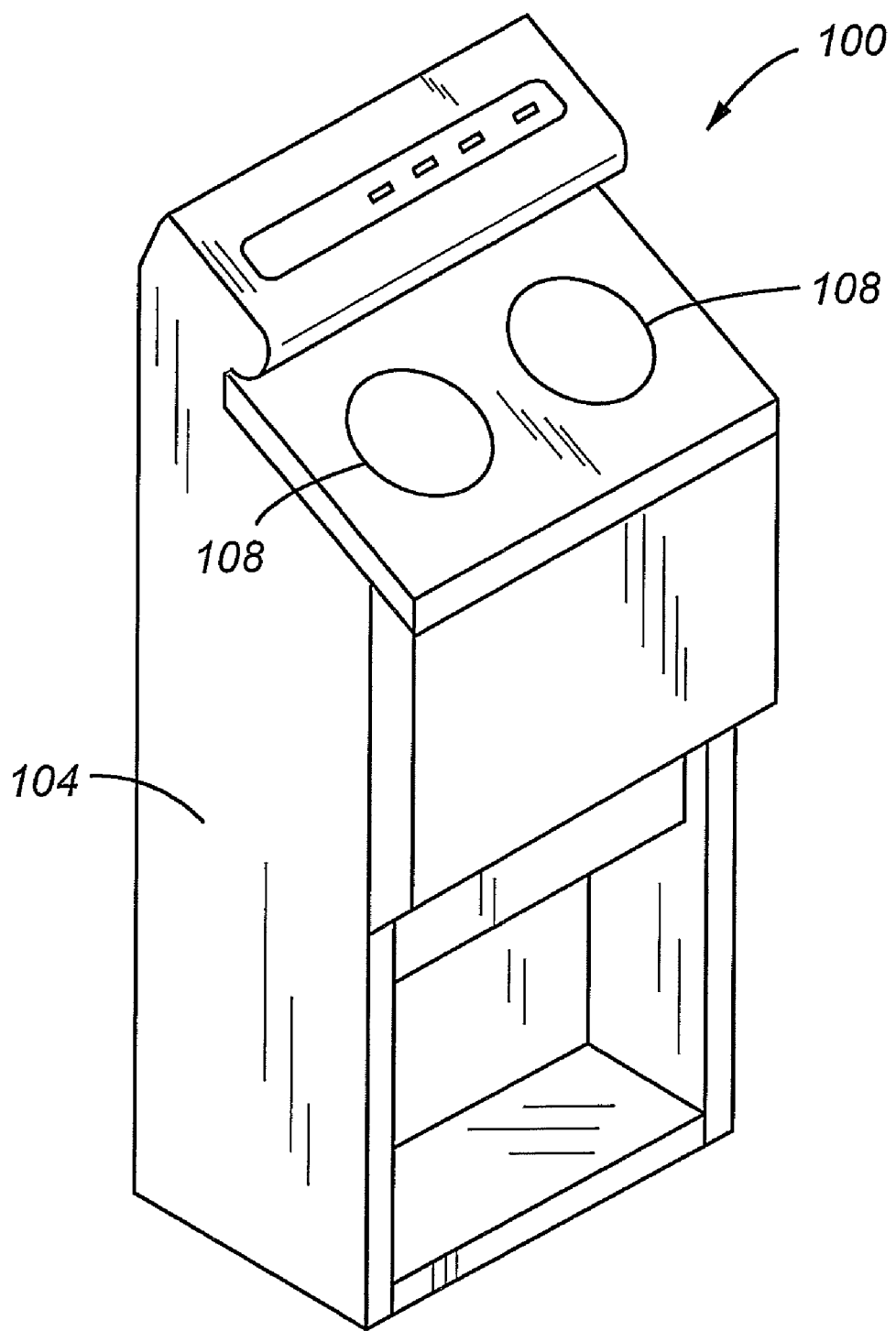
FIG. 1 is a perspective view of a cleaning station in accordance with embodiments of the present invention.

The drawings are not necessarily to scale, and may, in part, include exaggerated dimensions for clarity.

DETAILED DESCRIPTION

Embodiments of the present invention are directed to one or more elements of a system and method for providing automated washing of an appendage of a person. In addition, it is to be understood that embodiments of the present application are also applicable to other types of washing systems, including for example, boot-washing systems. In accordance with embodiments of the present invention, cleaning effectiveness can be improved from that of traditional sink and faucet systems, as well as existing automated cleaning stations by using an automated cleaning station with a novel wash cylinder construction. Various embodiments of the present invention are described in the following text and in the drawings; however, it is to be understood that examples described herein are not meant to be limiting. Accordingly, the scope of the present invention includes modifications and alternatives to the example embodiments described in text and shown in the figures associated herewith.

Cleaning stations operate to dispense one or more fluids, such as water, a cleaning fluid, such as soap, and/or a disinfectant, etc., while a person's hands are placed in a washbasin. As used herein, a "washbasin" or "wash chamber" means a structure associated with the cleaning station where an appendage, such as a hand (or foot/boot) are cleaned, such as one or more wash cylinders, spray areas, pans, tubs, etc. Individuals, such as employees of a laboratory, food service related industry, or health care facility, may be instructed to wash their hands for a minimum amount of time that has been determined to be sufficient to provide a complete cleaning. In situations where hand (or boot) washing is required, or because of personal preferences, the user may be required to use (or otherwise desire to use) an automated cleaning station that incorporates a wash cylinder.

Referring now to FIG. 1, an automated cleaning station 100 is depicted. The cleaning station 100 includes a body 104 and a pair of washbasins, and more preferably, cylinders 108 residing within the body 104 for receiving an object. As used herein an "object" may refer to anything cleaned by the automated cleaning station. An object may be, for example, an appendage of a user, a tool, a boot, and/or an inanimate object, etc. As used herein, "inanimate object" means an object that is principally not a biological tissue, although biological matter may be associated with the inanimate object, for example, a virus, bacteria, and/or pieces of tissue on a tool. For purposes of discussion, the various embodiments of the present invention are discussed herein in connection with cleaning an appendage of a user. However, it should be understood that the various embodiments may be used in connection with other objects.

The automated cleaning station 100 is shown as a free standing machine. Alternatively, the automated cleaning station 100 may be incorporated into a counter top, wall, or other structure. Embodiments of the present invention include at least one washbasin that comprises a cylinder 108 that rotates around a user's hand to clean the user's hand. Although referred to and shown as a "cylinder," the washbasin or wash chamber may comprise another shape. The cylinder may rotate either clockwise or counter-clockwise. Cleaning is performed by the application of fluids to the hands, wherein the fluids include water, a cleaning agent (such as soap), and/or a disinfectant, such as chlorhexidine gluconate (CHG). The fluids are directed toward the user's hands through a series of nozzles, wherein the nozzles provide coverage of cleaning fluids to the user's hand to clean and rinse the user's hand.

In use, the user inserts their hand into the cylinder 108 and the cleaning station 100 automatically initiates a cleaning cycle by reading the presence of the user's hand within the cylinder 104, such as by an optical sensor (not shown).

At least one embodiment of the present invention is directed to a novel wash cylinder for use in automated hand-washing machines. The rotating cylinder construction is especially effective in providing a complete hand washing in a quick and reliable manner. In that regard, the rotating cylinders may be provided with a plurality of nozzle sets, such as a three-set nozzle arrangement. At least one embodiment of the present invention features a novel orientation and arrangement of cylinder nozzles. Additionally, embodiments of the present invention include other novel features of a wash cylinder that provide for improved flow of water and/or cleaning fluid in and out of the cylinder.

When a person places his or her hands in the wash cylinders 108, they are washed and/or disinfected in a series of steps. Within approximately ten seconds the hands receive a (1) purge, (2) soap, and (3) rinse cycle. The purge cycle allows the water to reach the proper temperature. The soap cycle washes and allows the soap or disinfectant to kill germs. The rinse cycle removes the soap.

Figure 2A:
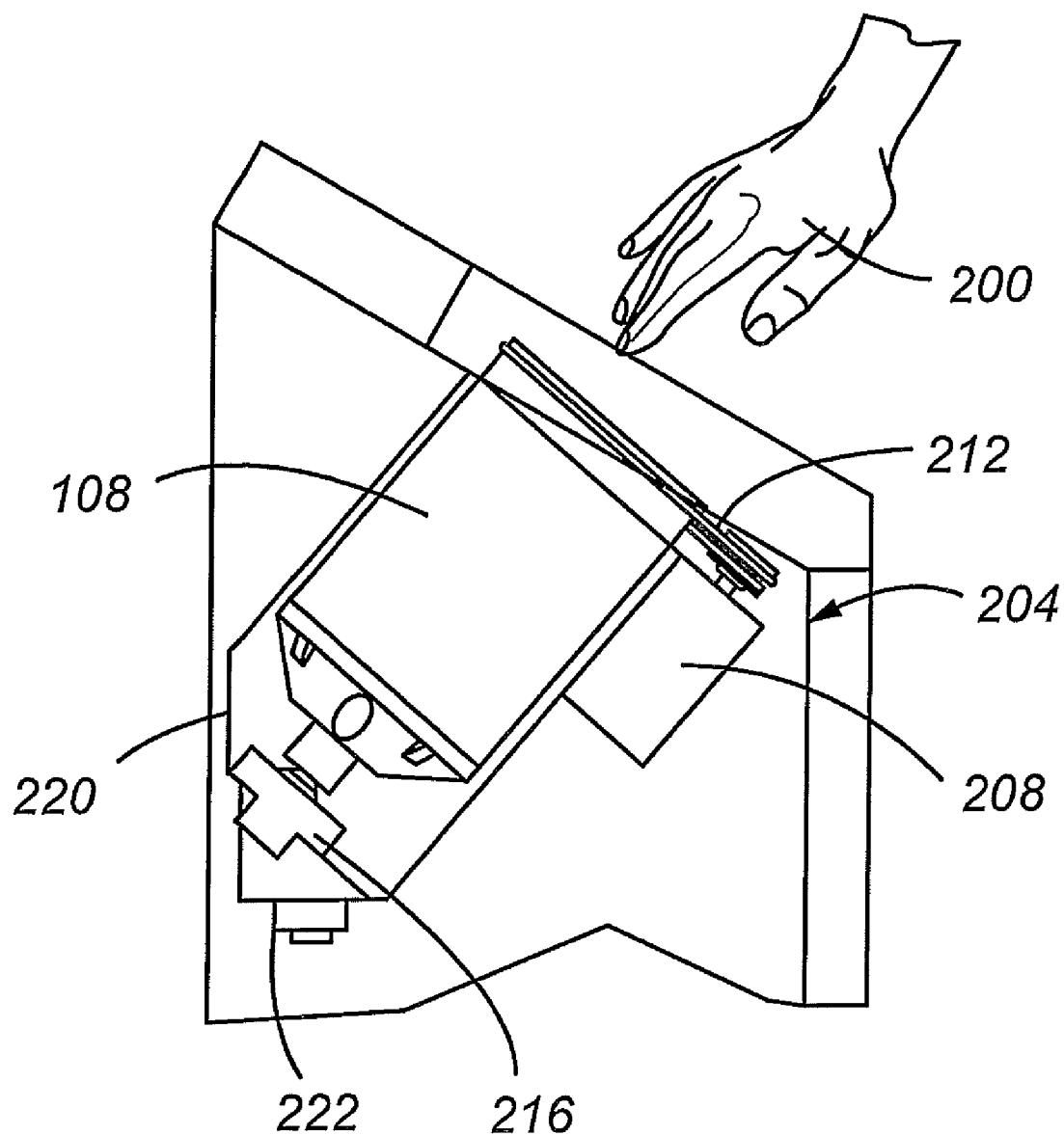
FIG. 2A is a schematic depiction of a portion of the cleaning station depicted in FIG. 1.

FIG. 2A provides a view of part of an exemplary automated cleaning station 100 used by an employee whose hand 200 is being placed in position to be washed. One wash cylinder 108 and other components associated with the wash cylinder 108 can be seen in FIG. 2A. The wash cylinder 108 may be associated with a drive assembly 204 including a drive mechanism 208 and a drive belt 212. The drive assembly 204 operates to rotate the wash cylinder 108 when the automated cleaning station 100 is in use. As the wash cylinder 108 rotates, a plurality of nozzles (not shown) disposed on the interior of the wash cylinder 108 spray water and/or cleaning fluid onto the hand 200. The wash cylinder 108 is interconnected to a seating assembly 216 that provides the wash cylinder 108 with a mounting within a receiving basin 220. As described in greater detail below, the receiving basin 220 receives spent water and/or cleaning fluid that drains out of the wash cylinder 108 after use in connection with washing or rinsing the hand 200. The spent fluid then exits through the basin drain 222 towards the sewer or other disposal system.

Figure 2B:
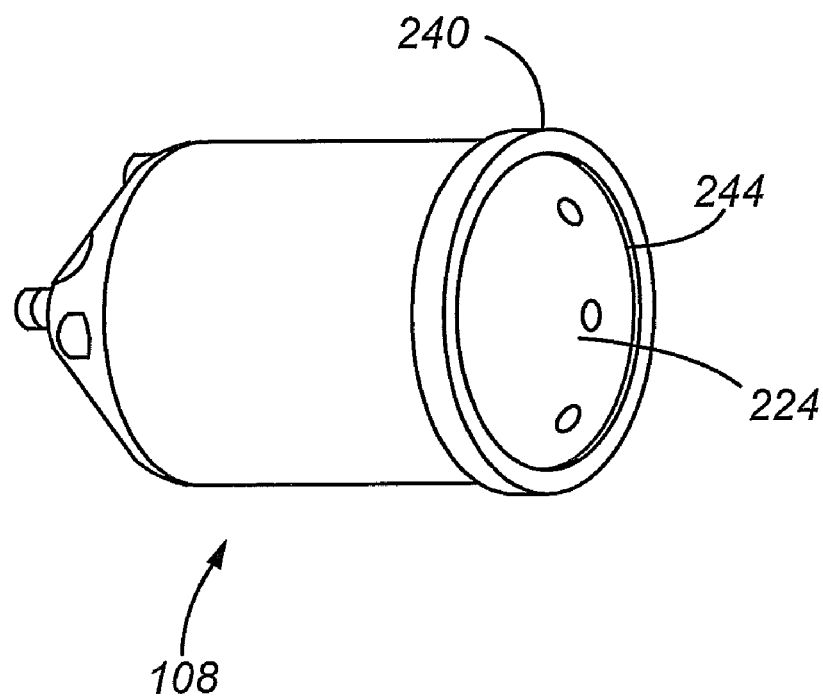
FIG. 2B is a perspective view of the wash cylinder shown in FIG. 2A.
Figure 2C:
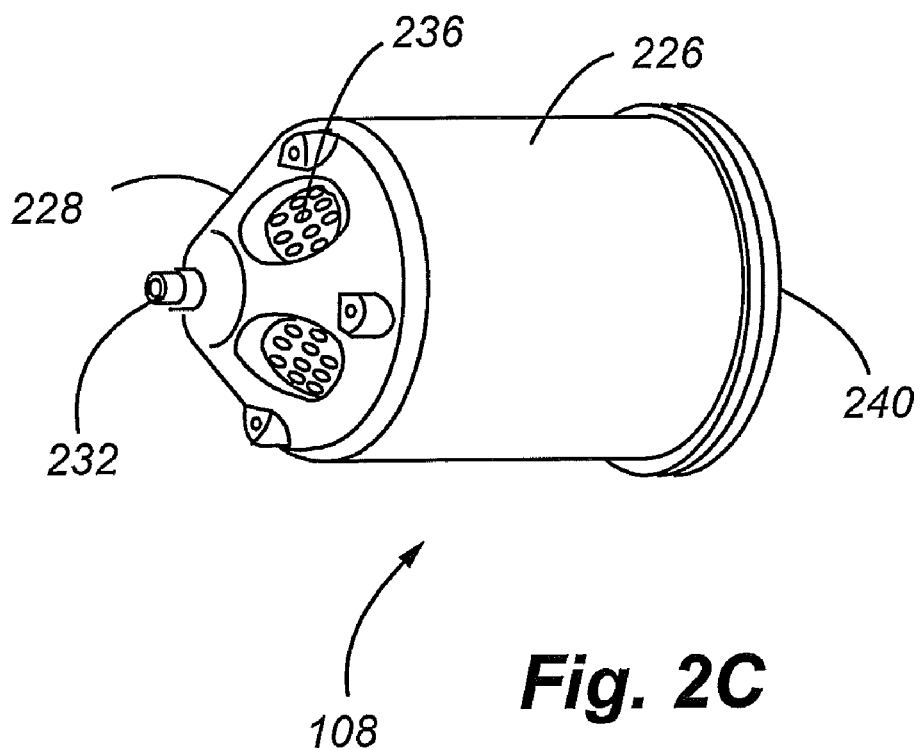
FIG. 2C is an additional perspective view of the wash cylinder shown in FIG. 2A.
Figure 2D:
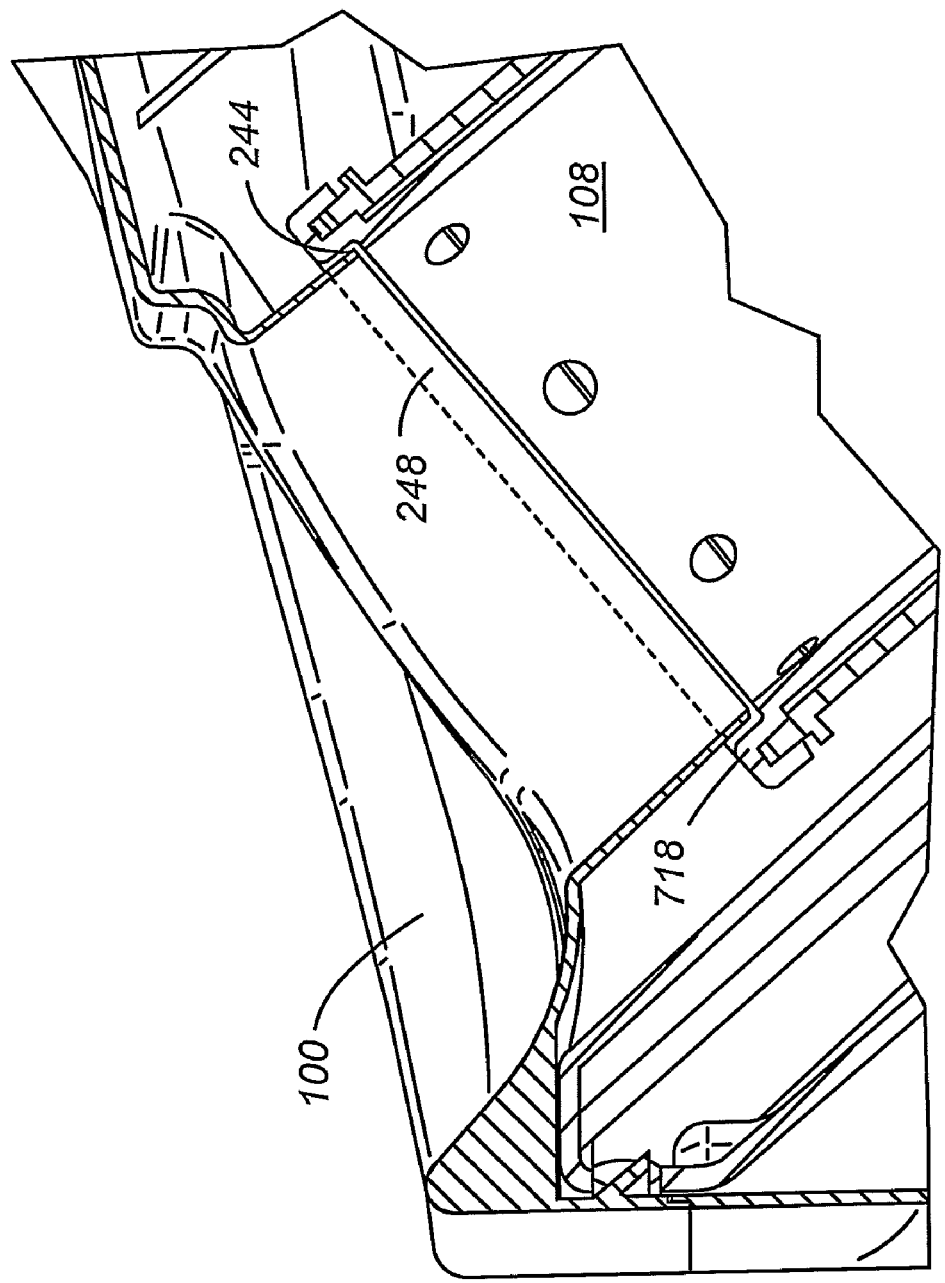
FIG. 2D is a close-up view of a portion of a cleaning station in accordance with embodiments of the present invention.

FIGS. 2B and 2C show detailed perspective views of the wash cylinder 108. The wash cylinder 108 includes an open end 224 and a frusto-conically shaped closed end 228. The closed end 228 includes a water inlet 232 and a plurality of drains 236. The open end 224 of the wash cylinder 108 features a rim 240 that includes a recessed portion 244. The recessed portion 244 is adapted to mate with a circular flange disposed on the automated cleaning station 100. The circular flange 248 can be seen with reference to FIG. 2D, which shows a close-up view of a portion of an automated cleaning station 100, including a top portion of the wash cylinder 108. As can be seen in FIG. 2D, the automated cleaning station 100 may include a circular flange 248 that is operatively associated with the recessed portion 244 of the cylinder. This arrangement prevents a person's fingers, and/or loose items, such as jewelry, from being caught between the rotating cylinder and non-moving portions of the automated cleaning station 100.

Figure 3A:
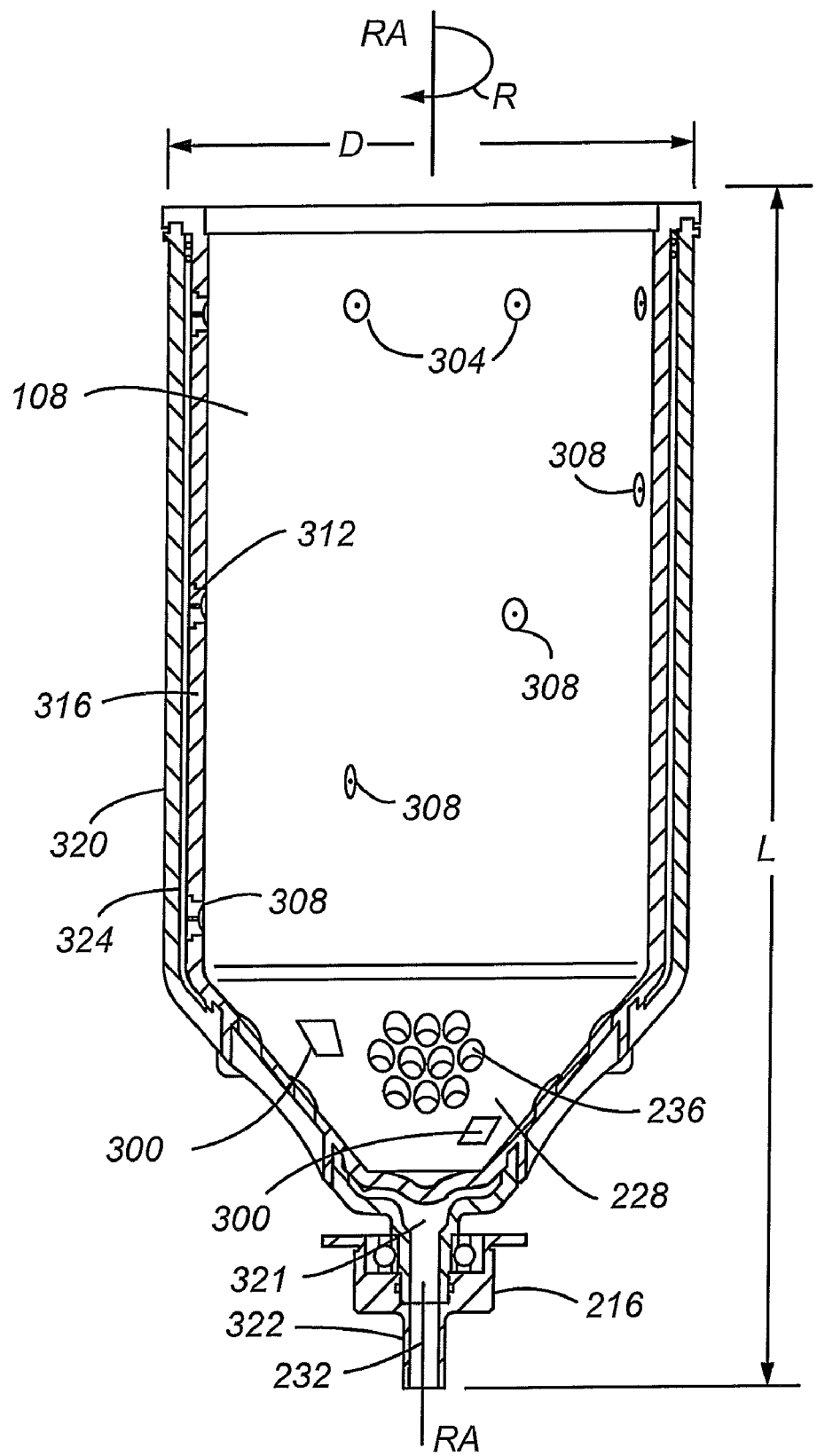
FIG. 3A is cross-sectional view of the wash cylinder and the seating assembly shown in FIG. 2A.
Figure 3B:
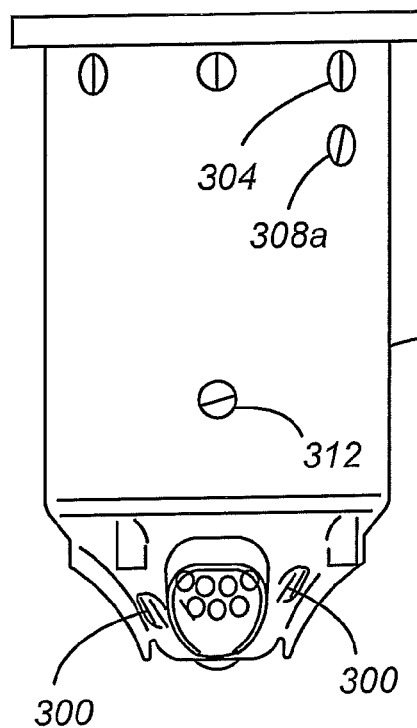
FIGS. 3 B-E are side elevation views of an inner cylinder in accordance with embodiments of the present invention.
Figure 3C:
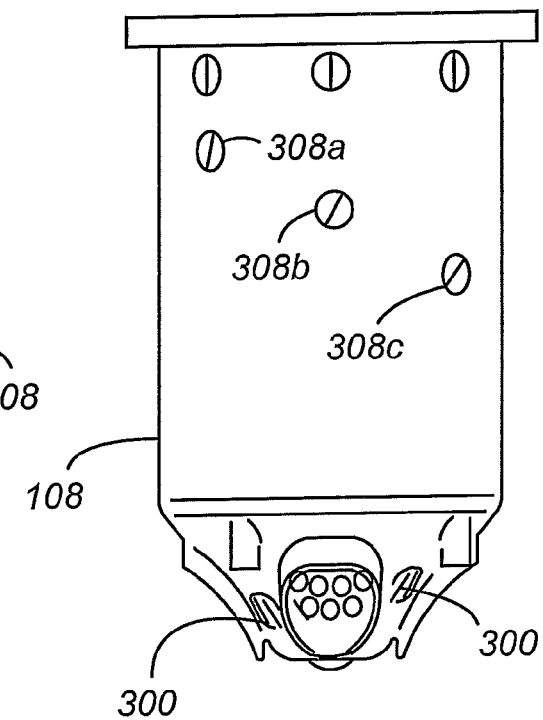
Figure 3D:
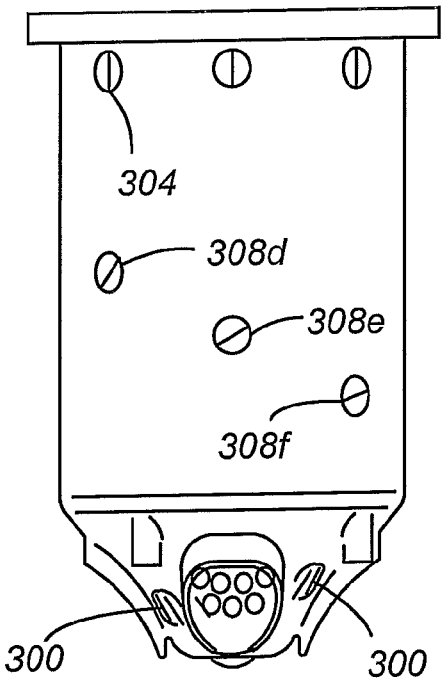
Figure 3E:
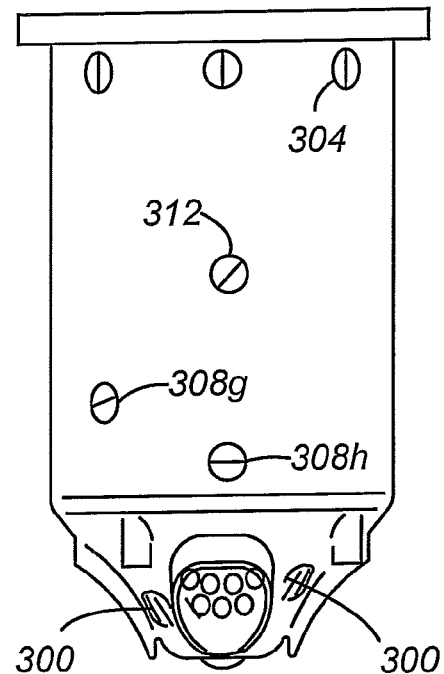

An understanding of the features of the appendage receiving member, such as wash cylinder 108, may be gained by an inspection of FIG. 3A, which depicts a cross-sectional view of the wash cylinder 108 and the seating assembly 216. Cylinder 108 preferably rotates around its rotational axis RA, such as in the direction of arrow R shown in FIG. 3A. At least one embodiment of the present invention includes nozzles arranged in a ring on the top end (the end proximate to the opening of the cylinder), nozzles arranged in a helical pattern along the length of the cylinder, one or more off-helix nozzles, and nozzles disposed on the bottom of the closed end of the cylinder. A portion of the complete arrangement of nozzles can be seen in FIG. 3A. In particular, bottom nozzles 300 are positioned on the closed end 228 of the wash cylinder 108. Top ring nozzles 304 are arranged just inside the open end 224 of the wash cylinder 108. Helical nozzles 308 are positioned in an array along the length of the wash cylinder 108. Four helical nozzles 308 are shown in FIG. 3A. However, it should be understood that the wash cylinder 108 may include additional helical nozzles 308 disposed on portions of the cylinder 108 that are not visible in the cross sectional view shown in FIG. 3A. In particular, the complete wash cylinder 108 may include any number of helical nozzles, such as for example, five, six, seven, eight, nine, or ten. Additionally, embodiments of the present invention include one or more off-helix nozzles 312.

As can be seen in FIG. 3A, the cylinder 108 includes or comprises an appendage receiving member having an inner member, such as inner cylinder 316, and an outer member, such as outer cylinder 320. The appendage receiving member and its inner and outer member (where present) may be cylindrical or substantially cylindrical in shape, or may comprise another shape. An annular cavity 324 is established between the inner cylinder 316 and the outer cylinder 320. By way of example and not limitation, the annular cavity 324 is preferably 0.070 inches wide. Alternatively, the annular cavity 324 may be between 1/16 inch and 3/16 inch wide. The length L of the wash cylinder 108 is preferably 11.490 inches. Alternatively, the length L of wash cylinder 108 may be between 12.5 and 10.5 inches. The diameter D of the wash cylinder 108 is preferably 6.580 inches. Alternatively, the diameter D of the wash cylinder 108 but may be between 7.5 and 5.5 inches. The above noted dimensions are example dimensions for a wash cylinder 108 used to clean a person's hands and are not meant to be limiting. Cylinders having different dimensions are within the scope of the present invention. For example, larger cylinders can be used to clean a person's hand, forearm and upper arm. Also, as those skilled in the art will appreciate, different sized cylinders can be used to clean a person's foot and/or lower leg.

The nozzles discussed above are disposed on the inner cylinder 316. A complete nozzle arrangement can be seen with reference to FIGS. 3B-E, each of which shows the same inner cylinder 316 from a different viewpoint. The embodiment of the present invention shown in FIG. 3B-3E shows a nozzle arrangement having eight helical nozzles 308a-h. The views shown in FIGS. 3B-E are 90 degrees apart, such that FIGS. 3B-E together show a complete 360 degree view of the inner cylinder 316. By way of illustration and not limitation, the inner cylinder 316 includes four bottom nozzles 300; eight top ring nozzles 304; eight helical nozzles 308a-h, and two off-helix nozzles 312. It should be understood that alternative embodiments of the present invention may include any suitable number of top ring nozzles, helical nozzles, off-helix nozzles and bottom nozzles.

In operation, the annular cavity 324 established between the inner cylinder 316 and the outer cylinder 320 is filled with water and/or cleaning fluid under pressure. Fluid enters the annular cavity 324 through the fluid inlet 232 disposed on the closed end 228 of the wash cylinder 108. As best seen in FIG. 3A, the fluid inlet 232 includes a circular hole 321 in the outer cylinder 320 and a tubular portion 322 depending therefrom. Within a short time after initiating a cleaning cycle, the annular cavity 324 fills and becomes pressurized. The pressure within the annular cavity 324 forces the fluid through the nozzles 300, 304, 308a-h and 312 and into the interior of the wash cylinder 108. As a result, a spray pattern is established in the interior of the wash cylinder 108. Fluid is removed from the wash cylinder 108 through the drains 236 disposed on the closed end 228. The spay pattern established in the interior of the cylinder 108 is discussed in greater detail below. In particular, embodiments of the present invention include a novel orientation and arrangement of nozzles that produce an advantageous spray pattern having greater coverage of the hand 200 and forearm of a user.

A more detailed understanding of the flow of fluid in and out of the wash cylinder 108 can be gained by an inspection of FIG. 4A, which shows a close-up view of the closed end 228 of an embodiment of a wash cylinder 108. Initially, as depicted by flow arrow 400, fluid enters through the fluid inlet 232. Then, as depicted by flow arrows 404a and 404b, the fluid flows into the annular cavity 324. It should be understood that as FIG. 4A is a cross-sectional view of the cylinder 108, only a portion of the fluid flow it depicted. In reality, the fluid flowing in from the inlet 232 spreads out in all directions to enter the annular cavity 324. When the annular cavity 324 fills and becomes pressurized, fluid is forced through the nozzles. The flow of fluid through one nozzle 308h is depicted in FIG. 4A. In particular, flow arrow 412 depicts flow into the nozzle 308h from the annular cavity 324, and flow arrow 416 depicts flow out of the nozzle 308h and into the interior of the wash cylinder 108. While FIG. 4A shows the flow of fluid through only one nozzle 308h, it should be understood that similar flow exists in other nozzles associated with the wash cylinder. After the fluid washes or rinses the hand 200, the fluid exits the wash cylinder 108 through the drains 236, as depicted by flow arrows 418. The spent fluid then enters the receiving basin 220 (shown in FIG. 2A) for drainage out of the system.

Figure 5:
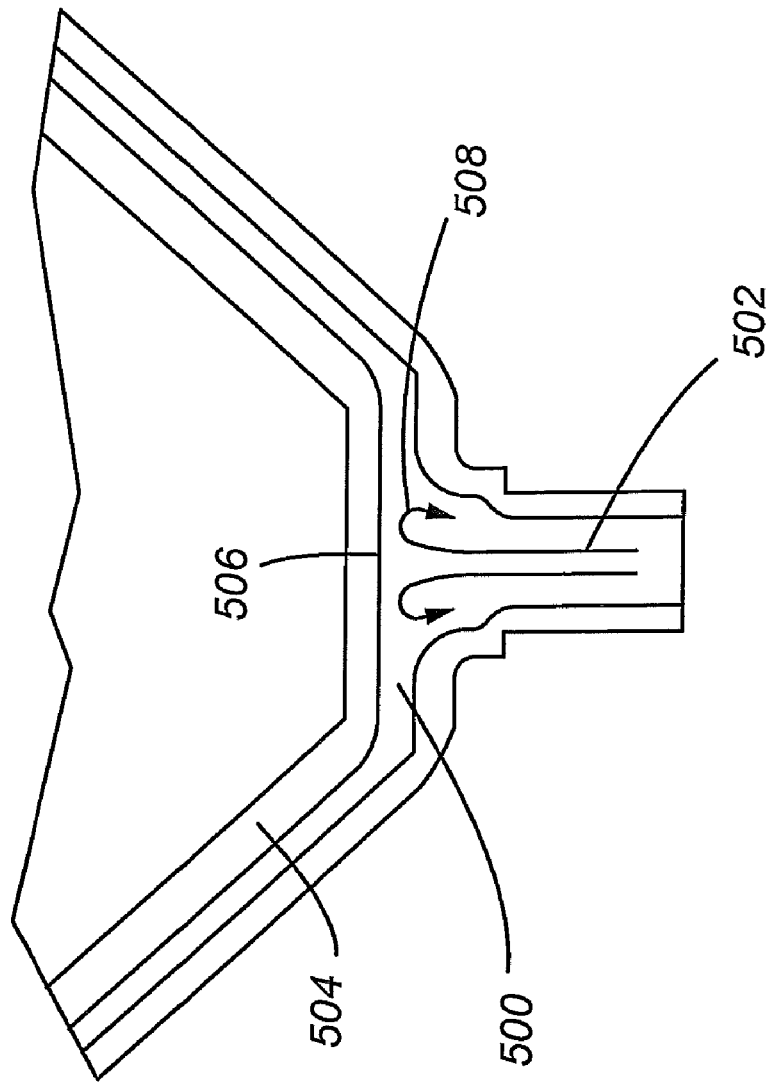
FIG. 5 is a cross-sectional view of a prior art wash cylinder.

Referring still to FIG. 4A, and in accordance with embodiments of the present invention, the tip of the closed end 228 of the inner cylinder 316 includes a flow guidance structure or protrusion 420. The protrusion 420 is disposed on the inner cylinder 316 in line with the inlet 232. Fluid is deflected radially by the protrusion 420 as it enters through the inlet 232 into the cavity 324 between the inner cylinder 316 and the outer cylinder 320. This deflection serves to direct the flow of fluid and leads to a decreased level of turbulence in the fluid. FIG. 5 depicts the situation that results from fluid entering a cavity 500 without being deflected radially. In particular, the fluid 502 flows perpendicularly into a surface 506 of an inner cylinder 504. As a result of the turbulence created 508, the fluid 502 does not flow smoothly. This leads to a loss of fluid pressure and a longer time needed to fill the cylinder.

Referring again to FIG. 4A, as a result of the fluid guidance structure or protrusion 420, the cavity between the inner cylinder 316 and the outer cylinder 320 is filled and pressurized faster. More specifically, the fluid guidance structure 420 includes a symmetrical sloped surface that has its greatest location of projection 421 disposed in line with a central axis around which the wash cylinder 108 rotates. As shown in FIG. 4B, sloped surface 436 of protrusion 420 is offset from the rotational axis RA of the cylinder 108 by an angle α, where angle α is less than 90°. The speed in which the cavity is filled is important for delivering a complete hand washing in a timely manner. In particular, the cleaning station 100 utilizes a number of different cycles, such as wash and rinse, that require different fluids to flow in and out of the cylinder. As a result, it is advantageous to fill and pressurize the cavity 324 quickly in order to provide a smooth and fast transition between cycles. Additionally, the overall time needed to complete the total number of cycles is important for providing a reliable handwashing. It has been shown that people are more likely to wash their hands if the handwashing can be accomplished in a short period of time. Accordingly, for a number of reasons, a reduction in the time needed to fill and pressurize the cavity 324, as accomplished by the protrusion 420, achieves an improved and more desirable handwashing.

Figure 6:
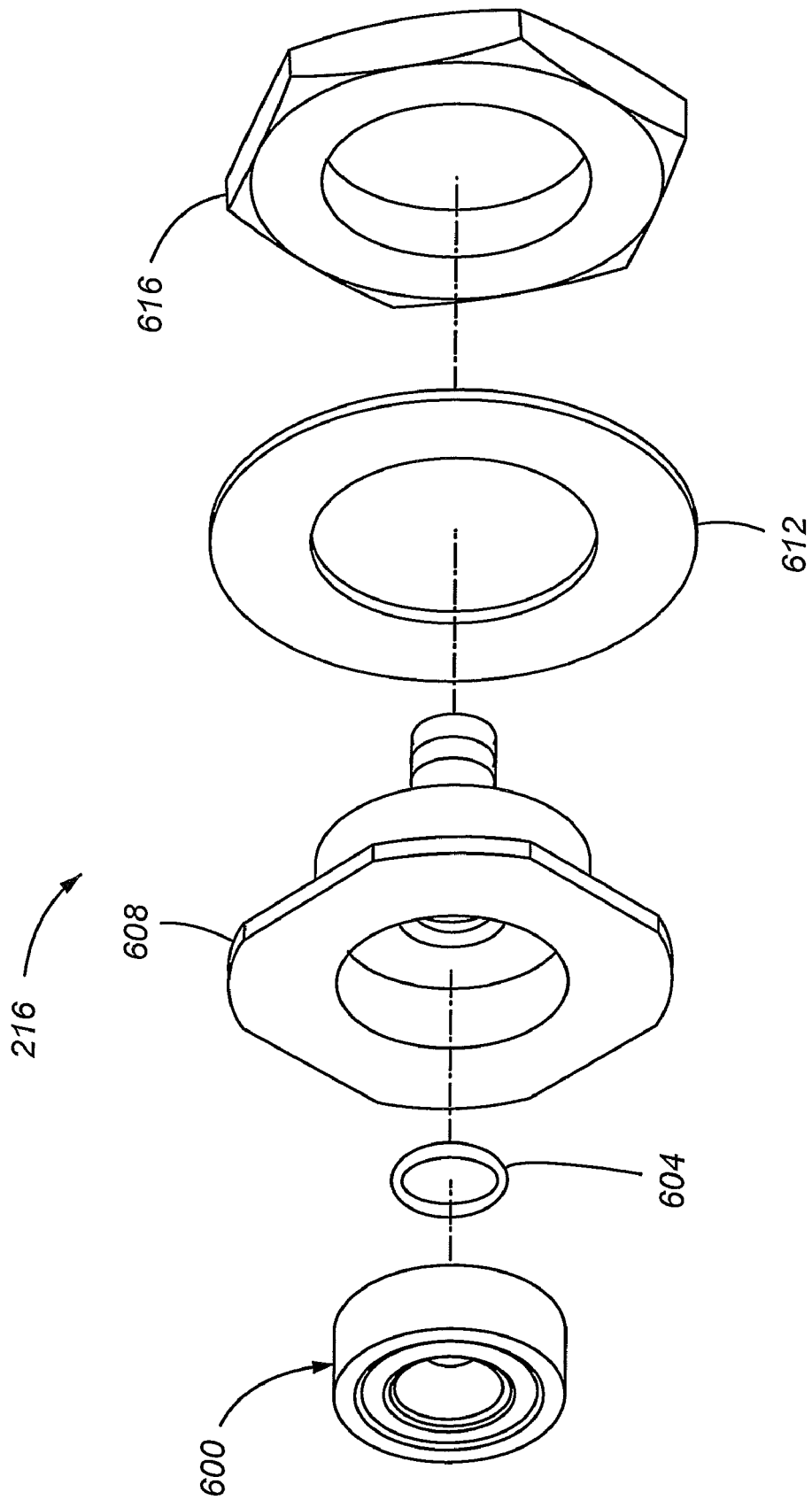
FIG. 6 is an exploded view of the seating assembly shown in FIG. 2A.

As spent fluid drains out of the wash cylinder 108 and into the receiving basin 220, the seating assembly 216 may become partially or totally submerged before the fluid exits through the basin drain 222. Accordingly, the seating assembly 216 is designed to operate in the presence of water and/or cleaning fluid. Components of the seating assembly 216 can be better seen in the exploded view shown in FIG. 6. As can be seen therein, the seating assembly 216 includes a bearing 600 and an O-ring 604 that are positioned within a bearing block 608. The bearing block is secured by means of a washer 612 and a panel nut 616 or other retaining hardware. The O-ring 604 operates to prevent fluid from entering the seating assembly 216. As a result, the connection between the wash cylinder 108 and the automated cleaning station 100 operates more effectively over a longer lifetime. Additionally, the O-ring 604 provides for a smoother connection when the cylinder 108 is mounted to the seating assembly 216, in comparison to previous friction-fit designs. Additionally, the O-ring 604 provides a seal between the bearing block 608 and the fluid inlet 232 preventing water and/or cleaning fluids from being lost in the receiving basin 220.

As described above, the appendage receiving member, such as wash cylinder 108, includes an inner member, such as inner cylinder 316, assembled to or integrated with an outer member, such as outer cylinder 320. As illustrated in the exploded view shown in FIG. 7, the wash cylinder 108 features a water tight seal between the inner cylinder 316 and the outer cylinder 320. In particular, the inner cylinder 316 includes protrusions 700 that contain holes 704 adapted to receive a connector, such as bolts or screws. The protrusions 700 are received in recessed portions 708 disposed on the outer cylinder 320. The inner cylinder 316 is interconnected to the outer cylinder 320 by screws that are driven through holes 712 in the recessed portions 708 into the holes 704 in the protrusions 700. Additionally, there are no hardware holes or protrusions on the inside of the inner cylinder that can cause harm to a user's hand. In accordance with embodiments of the present invention, the water tight seal between the inner cylinder 316 and the outer cylinder 320 may include other connecting mechanisms such as rivets and/or glue.

Additionally, in order to provide a water tight seal between the inner cylinder 316 and the outer cylinder 320, the outer cylinder 320 includes a flange 714 that is adapted for engagement with a lip 718 disposed on the inner cylinder 316. An O-ring (not shown) is positioned within the lip 718 to provide a seal between the inner cylinder 316 and the outer cylinder 320. The combination of the flange 714, lip 718 and the O-ring provides a seal that can resist high pressures exerted by fluid in the cavity between the cylinders 316 and 320. (The interconnection between the lip 718 and the flange 714 can be seen in FIG. 2D) Without this seal the cavity 324 may expand under high pressure conditions creating an opening between the cylinders 316 and 320 through which fluid may leak. A decreased fluid pressure will then be available at the nozzles and, accordingly, an inferior hand washing will result. Additionally, fluid leakage may result in unwanted fluid flow into portions of the automated cleaning station 100 that are unconnected to a drain 236 and/or are otherwise unable to receive fluid. Resulting fluid accumulation can lead to rust, electrical shorts, and/or other damage to components of the automated cleaning station 100. Accordingly, the seal structure described above provides a configuration that maintains fluid pressures and prevents undesirable leakage.

Figure 7:
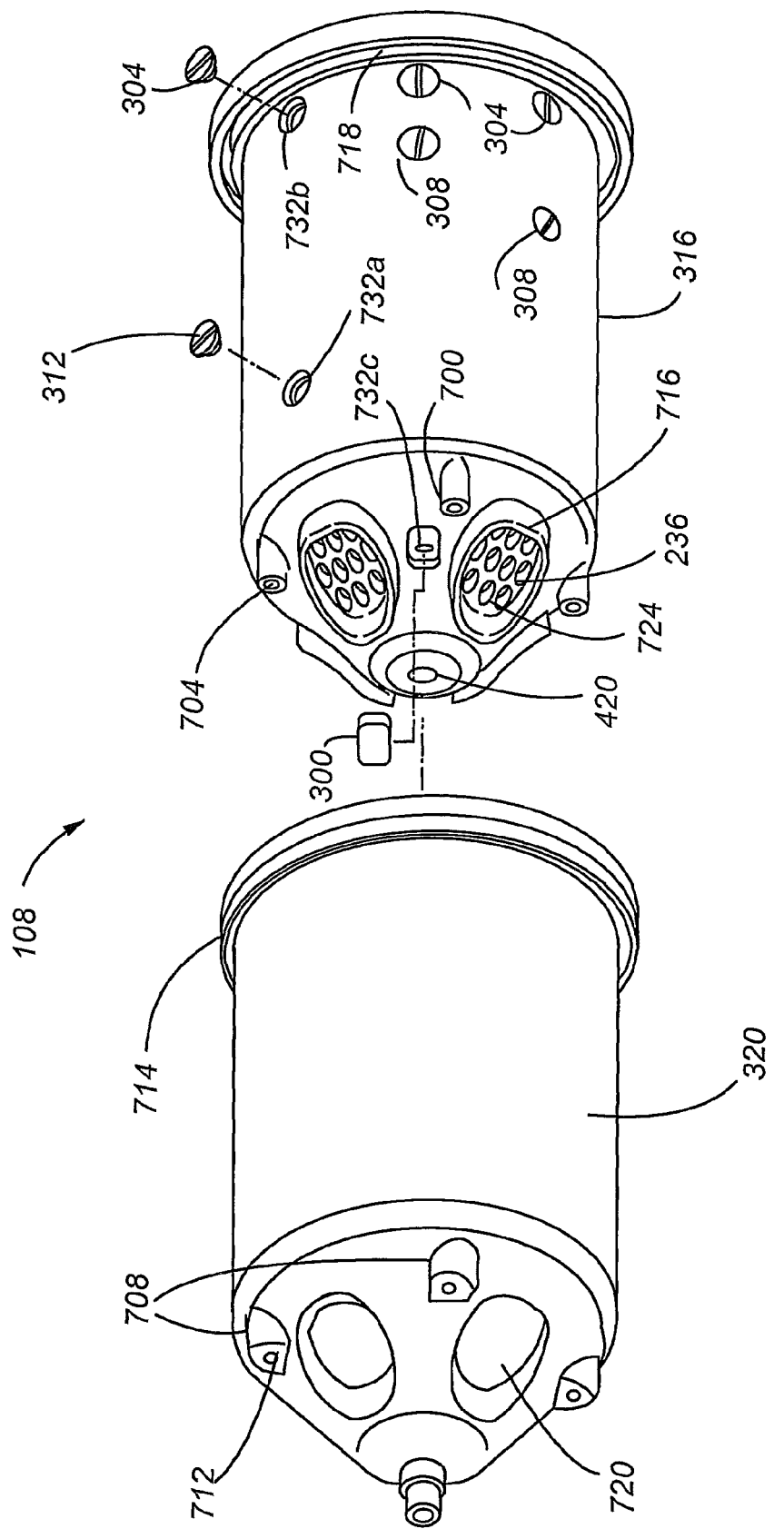
FIG. 7 is an exploded perspective view of a wash cylinder in accordance with an embodiment of the present invention.

Referring still to FIG. 7, the drains 236 are disposed on the inner cylinder 316 and include a drain wall 716. When the inner cylinder 316 is connected to the outer cylinder 320, each drain wall 716 is received in, and protrudes through a hole 720 in the outer cylinder 320. An O-ring (not shown) may be positioned around each drain wall 716 to provide a seal between the inner cylinder 316 and the outer cylinder 320. The surface of each drain 236 includes a plurality of perforations 724, which are large enough to allow fluid to pass through, and yet small enough to prevent a finger or small object from passing through. This drain configuration prevents a person's finger and/or their jewelry from being caught in the drain 236 when the wash cylinder is in motion. In addition, the relatively small size of the perforations 724 prevents trash that may be deposited in the wash cylinder 108 from working its way into and clogging the drainage system.

As can be seen in the exploded view of FIG. 7, the nozzles associated with the wash cylinder 108 are connected to the inner cylinder 316. In particular, the inner cylinder 316 includes a plurality of shaped holes that are adapted to receive a nozzle of a particular shape. (Alternatively, the nozzle may simply be a slit in the in wall of the inner cylinder 316.) The top ring nozzles 304, the helical nozzles 308a-h and the off-helix nozzles 312 have a "hat-shaped" construction adapted to fit in a similarly shaped hole in the inner cylinder. As can be seen in FIG. 7, an off-helix nozzle 312 is shown removed from its shaped hole 732a. Additionally, a top ring nozzle 304 is shown removed from its shaped hole 732b. The bottom nozzles 300 have a "square" construction. As can be seen in FIG. 7, a bottom nozzle 300 can be seen residing in its shaped hole 732c.

Figure 8C:
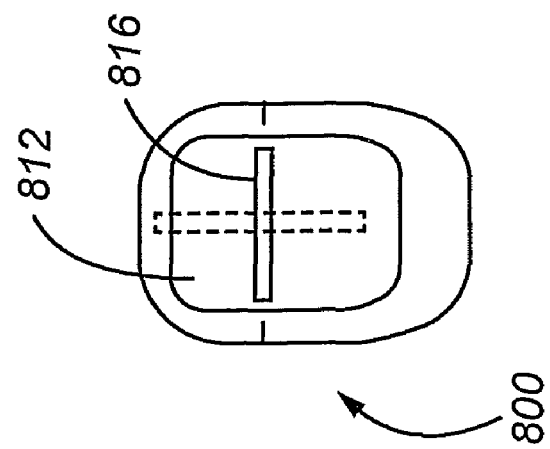
FIG. 8C is an elevation view of outlet side of a square nozzle.
Figure 8B:
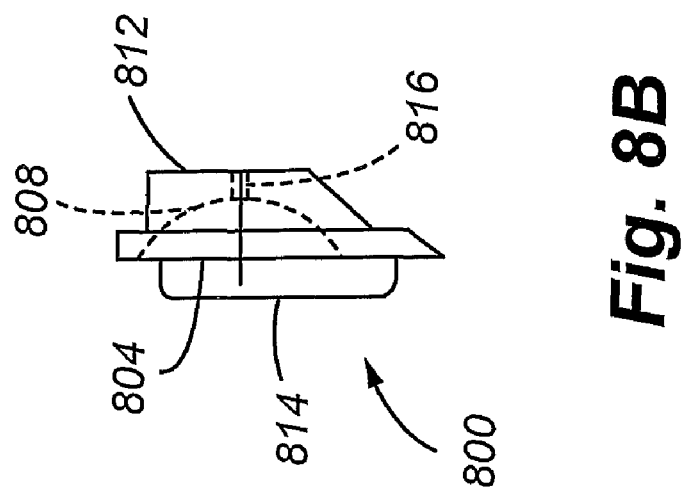
FIG. 8B is a side elevation view of a square nozzle.
Figure 8A:
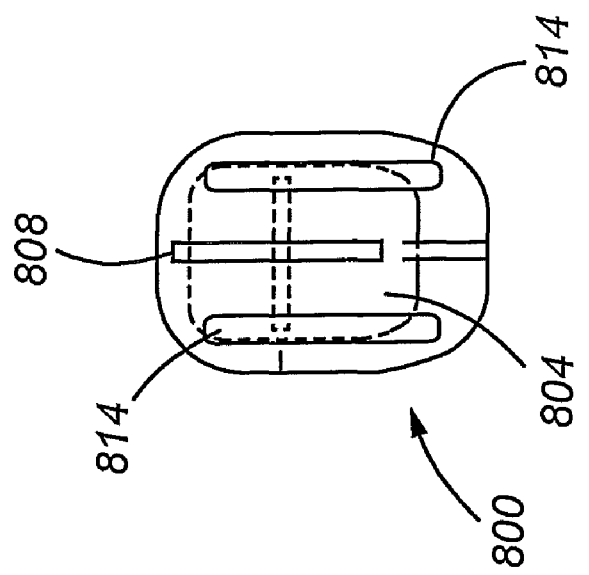
FIG. 8A is an elevation view of the inlet side of a square nozzle.

In accordance with embodiments of the present invention, the bottom nozzles 300 are implemented as square nozzles 800. The square nozzle 800 configuration is illustrated in FIGS. 8A-C. As can be seen, the square nozzle 800 includes an inlet side 804 having an inlet slot 808, and an outlet side 812 having an outlet slot 816. In at least one embodiment, the inlet slot 808 and the outlet slot 816 are perpendicular to each other. The square nozzle 800 has a shape that is adapted to be received in a similarly shaped nozzle hole 732c associated with the inner cylinder 316. When incorporated into the inner cylinder 316, the inlet side 804 is flush with the outer surface 424 of the inner cylinder 316, and the outlet side 812 is flush with the inner surface 428 of the inner cylinder 316. In operation, the water and/or cleaning fluid flows from the annular cavity 324 through the slots 808 and 816 of the square nozzle 800. The bottom nozzles 300 are placed in a position wherein their spray may directly impact the fingernails and finger tips of the hand.

The bottom nozzles 300, shown in FIG. 8A-C, include ribs 814 disposed on the inlet side 804 of nozzle 800. The ribs 814 prevent the nozzle from being pushed out and dislodged during operation of the wash cylinder. In particular, the ribs 814 engage the inner wall 432 of the outer cylinder 320 when the inner cylinder 316 is installed in the outer cylinder 320. In accordance with embodiments of the present invention, any of the nozzles disclosed herein may incorporate a one or more ribs 814.

In accordance with embodiments of the present invention, the wash cylinder 108 may incorporate both a "straight" type nozzle and an "angled" type nozzle, both of which have a hat-shaped construction, as described above. As described in greater detail below, the difference between the straight nozzle and the angled nozzle is in the orientation of internal slots that form a passageway in which fluid travels from the inlet side to the outlet side. Both the straight and the angled nozzles produce a flat "fan" spray pattern that emerges at a small-area opening on the outlet side and spreads out through an angle while remaining substantially in one plane. However, as result of the differing internal slot orientations, the angle at which the fan spray emerges from the straight nozzle 900 (described in connection with FIGS. 9A-C) is different from the angle at which the fan spray emerges from the angled nozzle 1000 (described in connection with FIGS. 10A-C).

Figure 9C:
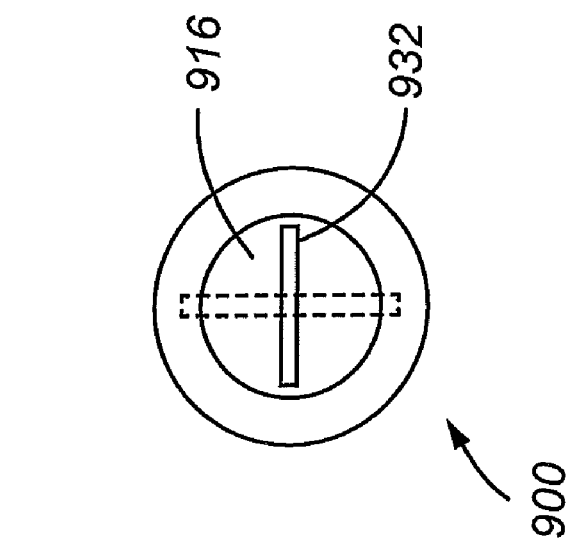
FIG. 9C is an elevation view of outlet side of a straight nozzle.
Figure 9B:
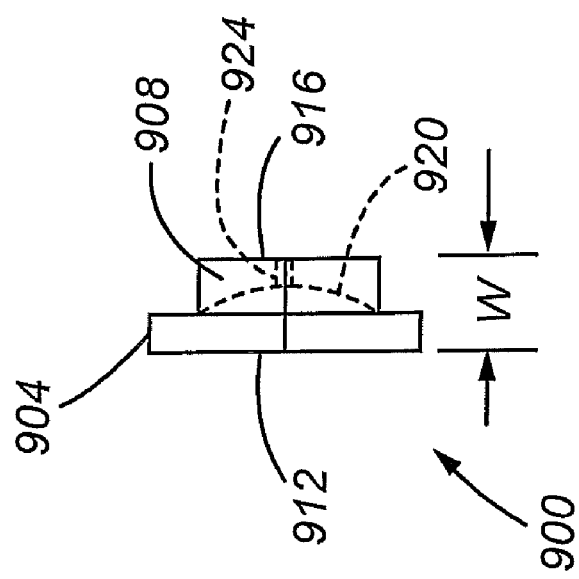
FIG. 9B is a side elevation view of a straight nozzle.
Figure 9A:
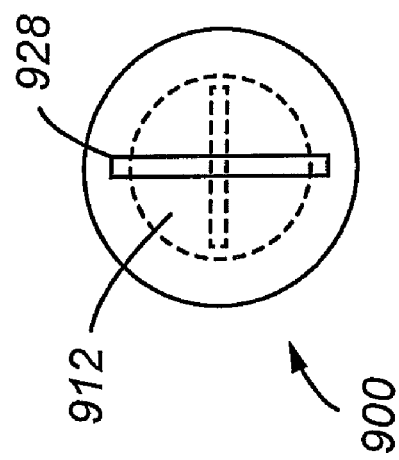
FIG. 9A is an elevation view of the inlet side of a straight nozzle.

An exemplary straight nozzle 900 designed to be received in the shaped holes 732a, is illustrated in FIGS. 9A-C. The straight nozzles 900 include a first or larger-diameter disk 904 integrated with or interconnected to second or smaller-diameter disk 908. The inlet side 912 of the straight nozzle 900 corresponds to the outside face of the larger-diameter disk 904. The outlet side 916 of the straight nozzle 900 corresponds to the outside face of the smaller-diameter disk 908. As best seen in FIG. 4A, when incorporated into the inner cylinder 316, the inlet side 912 is flush with the outer surface 424 of the inner cylinder 316, and the outlet side 916 is flush with the inner surface 428 of the inner cylinder 316.

Still referring to FIG. 9A-C, the straight nozzle 900 features two intersecting circular shaped slots 920 and 924 that together form a passageway through which fluid may travel. As best seen in FIG. 9B, the inlet slot 920 begins on the inlet side 912 and continues through a portion of the width W of the straight nozzle 900. The outlet slot 924 begins on the outlet side 916 and continues through a portion of the width W of the straight nozzle 900 such that an intersection is provided with the inlet slot 920. As can be seen in FIG. 9A, the inlet slot 920 includes a thin rectangularly-shaped inlet opening 928 in the inlet side 912 of the straight nozzle 900. Similarly, as can be seen in FIG. 9C, the outlet slot 924 includes a thin rectangularly-shaped outlet opening 932 in the outlet side 916 of the straight nozzle 900. As can be seen, the inlet opening 928 and the outlet opening 932 are approximately perpendicular. In operation, the fan spray produced by the straight nozzle 900 emerges at a 90 degree angle with respect to the outlet side 916 of the straight nozzle 900. In accordance with embodiments of the present invention, the helical nozzles 308a-h and the off-helix nozzles 312 are implemented as straight nozzles 900.

FIG. 10A through FIG. 10C provide illustrations of the angled nozzle 1000. As can be seen, the angled nozzle 1000 includes the hat-shaped construction described above, including a larger diameter disk 1004 and a smaller diameter disk 1008. The angled nozzle additionally includes an inlet side 1012 and an outlet side 1016. Similar to the straight nozzle 900, the angled nozzle 1000 features two intersecting circular shaped slots 1020 and 1024 that together form a passageway through which fluid may travel. As best seen in FIG. 10B, the inlet slot 1020 begins on the inlet side 1012 and continues through a portion of the width W of the angled nozzle 1000. The outlet slot 1024 begins on the outlet side 1016 and continues through a portion of the width W of the angled nozzle 1000 such that an intersection is provided with the inlet slot 1020. In contrast to the straight nozzle 900, the angled nozzle 1000 includes an outlet slot 1024 disposed at an angle θ with respect to the axis A of the nozzle 1000. By way of example and not limitation, the angle between the outlet slot 1024 and the axis A is preferably 15 degrees. In accordance with another embodiment of the present invention, the angle between the outlet slot 1024 and the axis A may be between 5 and 30 degrees. In accordance with yet another embodiment of the present invention, the angle between the outlet slot 1024 and the axis A may be between 1 and 90 degrees. With reference to FIG. 10A, the inlet slot 1020 includes a thin rectangularly shaped inlet opening 1028 in the inlet side 1012 of the angled nozzle 1000. Similarly, as can be seen in FIG. 10C, the outlet slot 1024 terminates in a thin rectangularly shaped outlet opening 1032 in the outlet side 1016 of the angled nozzle 1000. As can be seen, the inlet opening 1028 and the outlet opening 1032 are approximately perpendicular. By way of example and not limitation, as a result of the 15 degree angle of the outlet slot 1024, the fan spray produced by the angled nozzle 1000 emerges at a 75 degree angle with respect to outlet side 1016 of the angled nozzle 1000. In accordance with embodiments of the present invention, the top ring nozzles are implemented as angled nozzles 1000. The top ring nozzles 304 (shown in FIG. 3A) are angled into the interior of the cylinder such that they provide a fluid "curtain" that minimizes the spraying and splashing of fluid out of the cylinder 108 and provides washing at the wrist of the hand 200.

The nozzle holes 732a-c may be a particular shape that is adapted to receive a particular nozzle. For example, nozzles holes 732a-b are adapted to receive hat-shaped nozzles (either a straight nozzle 900 or an angled nozzle 1000) and may include a smaller diameter portion adapted to fit only the smaller diameter-disk 904, 1004. Accordingly, it is only possible to insert the nozzle in one direction. Additionally, when different types of nozzles are used (e.g. straight nozzles 900 and angled nozzles 1000), the top ring nozzles 304 may be of a different size than the helical nozzles 308a-h. Accordingly, the nozzle holes 732b associated with the top ring nozzles 304 are of a different size than the nozzle holes 732a associated with the helical nozzles 308a-h. Accordingly, a nozzle to be used in connection with helical nozzle 308a-h may not be inadvertently placed in a nozzle hole 732b adapted to receive a top ring nozzle 304, and vice versa. These nozzle features provide ease for manufacturing while improving quality of flow because the nozzles are located in their proper position.

When incorporated into the inner cylinder 316, a particular nozzle (straight nozzle 900 or angled nozzle 1000) does not extend away from the inner surface 428 of the wash cylinder 108. Accordingly, they do not present any protrusions that would contact the hand during a wash. Additionally, as the nozzles 900, 1000 are not angled with respect to the wall of the cylinder, the width of the cavity may be manufactured at a smaller width than was possible in previous designs. Additionally, the complexity of the mold tool of assembly and cylinder is decreased.

As mentioned above, straight nozzles 900 (typically used to implement the helical nozzles 308a-h and the off-helix nozzles 312) and the angled nozzles 1000 (typically used to implement the top ring nozzles 304) both have a hat-shaped configuration that allows them to be fit in a nozzle hole 732a-b. In accordance with an alternative embodiment of the invention, a plurality of nozzles may be integrally formed within a single nozzle "inlay," in order to provide greater ease in assembling a wash cylinder 108. FIGS. 11A-C depict an example of a nozzle inlay 1100 in accordance with embodiments of the present invention. In particular, FIGS. 11A-C show the exterior structure of a nozzle inlay 1100 having five nozzles 1102. Alternatively, the nozzle inlay 1100 may have a different number of nozzles, such as two, three, four, six or seven. In one embodiment, the nozzle inlay 1100 has a single relatively long nozzle (not shown). The nozzle inlay 1100 has an inlet side 1104 and an outlet side 1108. FIGS. 12A-C show the internal structure of the nozzle inlay 1100, including inlet slots 1204 and outlet slots 1208. While the nozzle inlay 1100 shown in FIGS. 11A-C and FIGS. 12A-C includes nozzles of the straight type, it should be understood that nozzle inlays that include nozzles of the angled type are within the scope of the invention.

Figure 13:
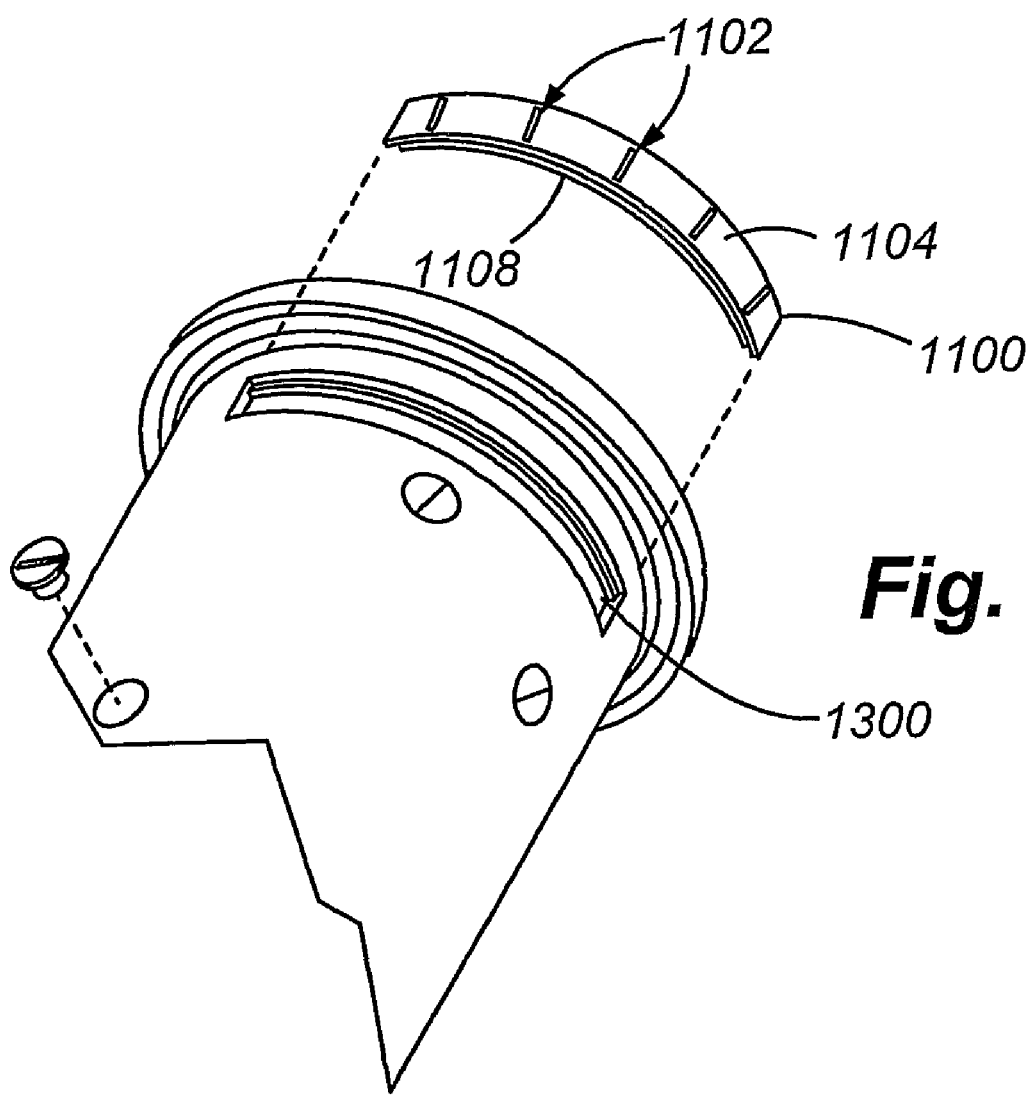
FIG. 13 is a perspective view of a nozzle inlay attached to a wash cylinder.

As shown in FIG. 13, wash cylinders 108 that incorporate nozzle inlays preferably include a channel or recessed portion 1300 that is adapted to receive the nozzle inlay 1100. Accordingly, multiple nozzles may be installed in the cylinder 108 in one step. When incorporated into the inner cylinder 316, the inlet side 1204 is flush with the outer surface 424 of the inner cylinder 316, and the outlet side 1208 is flush with the inner surface 428 of the inner cylinder 316.

FIG. 14A and FIG. 14B depict various nozzle inlays incorporated into an inner cylinder 316. For the exemplary embodiments of the inner cylinders depicted therein, the inner cylinder 316 may include a curved type nozzle inlay 1400 that is disposed perpendicular to the axis of the cylinder, and a straight type nozzle inlay 1404 that is disposed parallel to the axis of the cylinder.

In accordance with embodiments of the present invention, the helical nozzles 308*a-h* may be implemented with straight nozzles 900 and each nozzle disposed at a different angular orientation in order to provide a spray pattern having improved coverage of the user's hand and forearm. In particular, the helical nozzles 308*a-h* may be disposed at different angular orientations around the axis A of the nozzle to produce a variety of different angled spray patterns. The different angular orientations are achieved by the placement of the helical nozzles 308*a-h* at different angles within its nozzle hole 732*a*. Alternatively, when nozzle inlays 1100 are used, the different angular orientations of the nozzles may be built into the nozzle inlay 1100 itself.

The spray pattern produced by disposing a straight nozzle 900 at an angular orientation with respect to its axis A is different from the spray pattern produced by the angled nozzle 1000. In order to more clearly describe this distinction, a "pitch" and a "roll" angle are defined. As used herein, the "pitch angle" is described as being the angle away from the axis of the nozzle. A "roll angle" is defined as being around the axis A of the nozzle. The internal structure of the nozzles determines the pitch angle of the spray pattern that is produced. In particular, the angled slots 1020 and 1024 of the angled nozzle 1000 result in a spray pattern having, for example, a 15 degree pitch angle. Similarly, the orientation of the internal slots 920 and 924 of the straight nozzle 900 result in spray pattern having a 0 degree pitch angle. In contrast, the roll angle is determined by the orientation in which the nozzle is placed in its nozzle hole 732*a*. As used herein, a nozzle oriented such that its outlet opening 932 or 1032 lies in a plane parallel to a plane defined by the opening of the cylinder 108 has a spray pattern with a 0 degree roll angle.

Referring again to FIGS. 3B-E, the nozzles depicted therein produce spray patterns having various pitch and roll angles. As mentioned above, the top ring nozzles 304 may be implemented with angled nozzles 1000. Furthermore, as can be seen, the nozzles 304 are oriented such that their inlet openings 1028 are "vertical." As can be appreciated from the discussion in connection with FIGS. 10A-C, their outlet openings 1032 are then "horizontal" or, equivalently, in a plane parallel to a plane defined by the opening of the cylinder 108. Accordingly, and by way of example and not limitation, each nozzle 304 produces a fan spray having a 15 degree pitch angle and a 0 degree roll angle. Also as mentioned above, the helical nozzles 308*a-h* may be implemented using straight nozzles 900. As can be seen from FIGS. 3B-E, the nozzles 308*a-h* are oriented at various rotational angles. Accordingly, the helical nozzles 308*a-h* produce fan sprays having 0 degree pitch angle and various roll angles.

In accordance with embodiments of the present invention, orienting the nozzles 308*a-h* at progressively steeper roll angles produces a combined spray pattern that produces an improved coverage of the hand and forearm and results in a thorough hand washing. Additionally, the off-helix nozzles 312 provide for an improved coverage of the hand and forearm. As shown in FIGS. 3B-E, the helical nozzle 308*a* has a roll angle of approximately 0 to 10 degrees. Generally, the helical nozzle 308*a* may be disposed at shallow angle defined herein as being between 0 degrees and 45 degrees. The helical nozzle 308*b* has a roll angle of approximately 10 to 20 degrees. Continuing in this manner, it can be appreciated that helical nozzles 308*c-g* have progressively steeper roll angles, ending with helical nozzle 308*h* which has a roll angle of approximately 80 to 90 degrees.

Figure 15A:
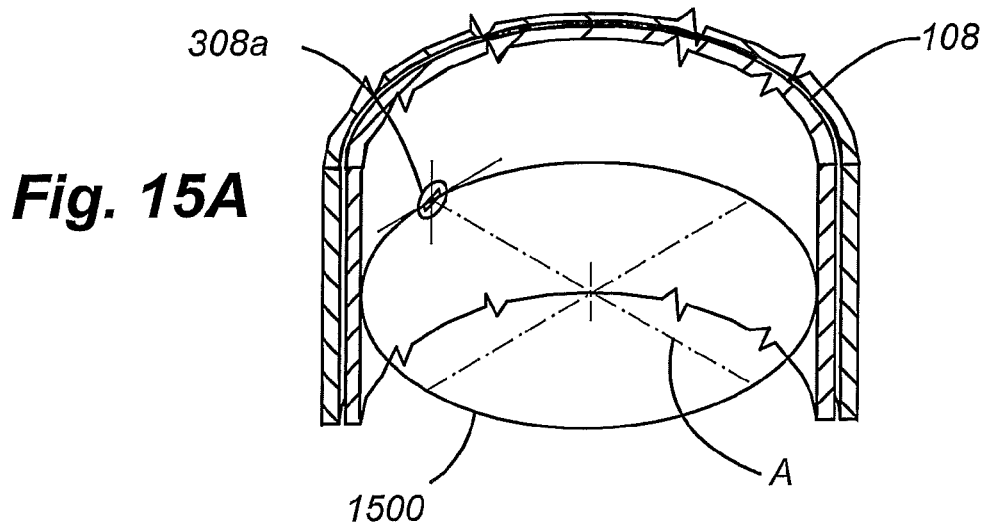
FIGS. 15A-C are perspective views of the spray pattern produced by helical nozzles in accordance with embodiments of the present invention.
Figure 15B:
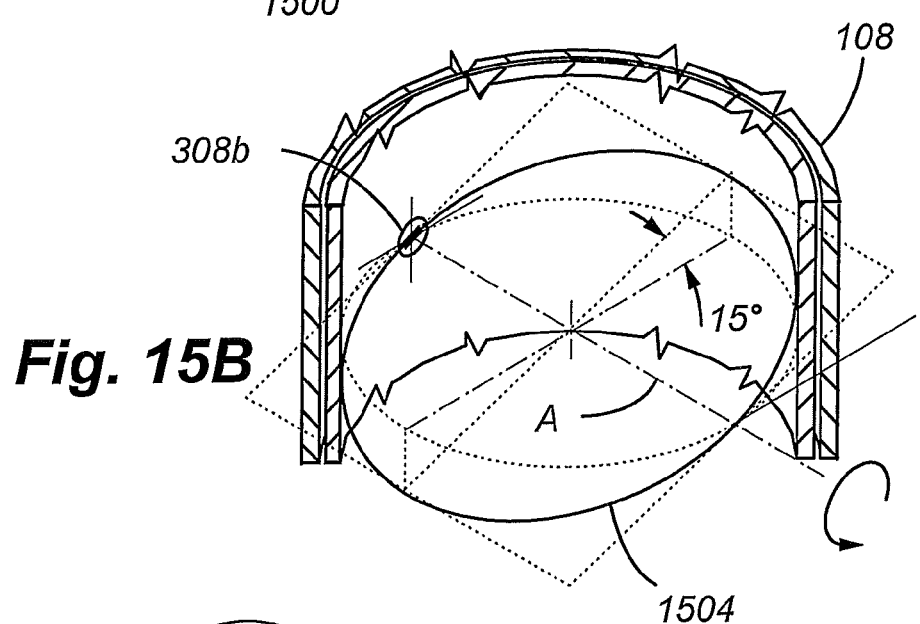
Figure 15C:
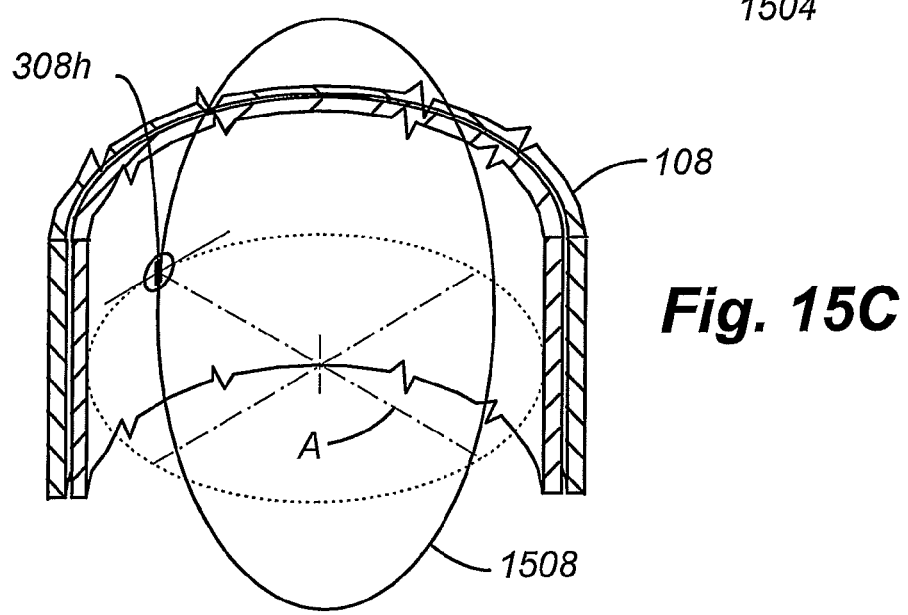
Figure 15D:
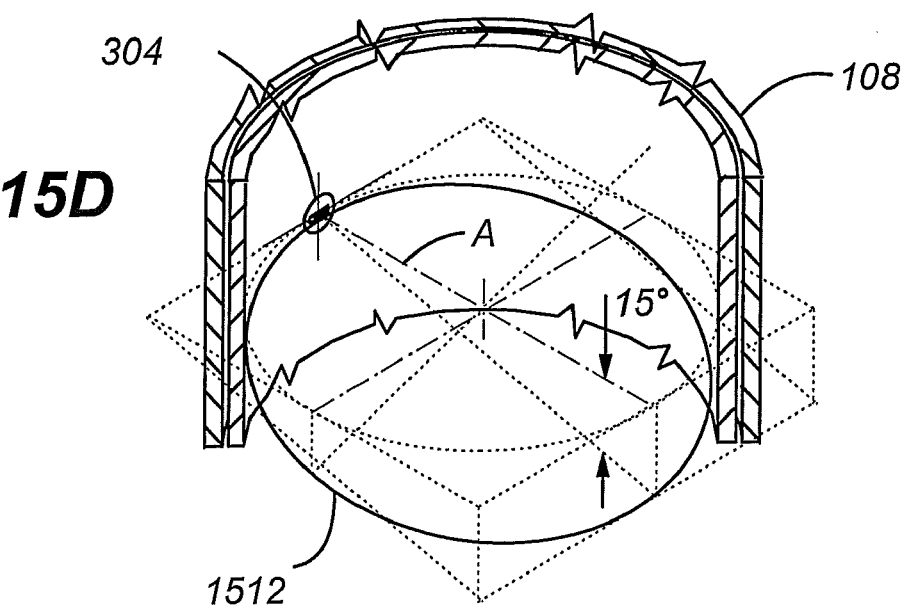
FIG. 15D is a perspective view of the spray pattern produced by a top ring nozzle in accordance with embodiments of the present invention.

In order to further clarify the spray pattern produced in the wash cylinder 108, FIGS. 15A-D show individual spray patterns produced by various nozzles. In particular, FIG. 15A shows the spray pattern 1500 produced by the helical nozzle 308*a*. As can be seen, the spray pattern produced by this nozzle has 0 degree pitch angle and approximately a 0 degree roll angle. FIG. 15B shows the spray pattern 1504 produced by helical nozzle 308*b*, which has a 0 degree pitch angle and a 15 degree roll angle. FIG. 15C shows the spray pattern 1508 produced by nozzle 308*h*, which has a 0 degree pitch angle and a 90 degree roll angle. FIG. 15D shows the spray pattern 1512 produced by the top ring nozzle 304, which has 15 degree pitch angle and a 0 degree roll angle. An appreciation of the difference between the pitch and roll angles may be gained by a comparison of FIG. 15B, which shows helical nozzle 308*b* having a 0 degree pitch angle and a 15 degree roll angle, with FIG. 15D shows top ring nozzle 304 having a 15 degree pitch angle and a 0 degree roll angle.

Figure 16A:
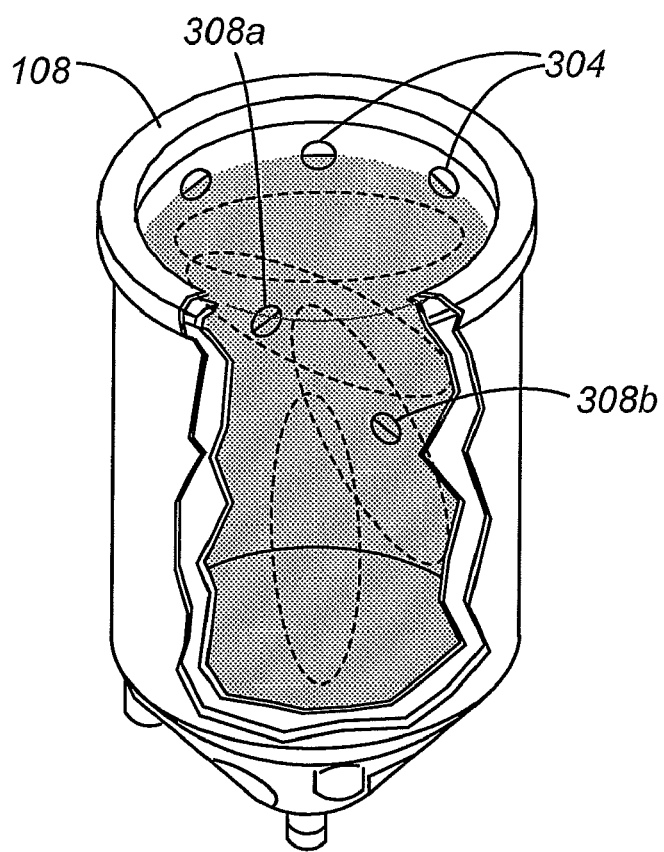
FIG. 16A is a cut-away perspective view of the combined spray pattern produced by an exemplary nozzle arrangement in accordance with embodiments of the present invention.

FIG. 16 shows a simplified illustration of the combined spray pattern that results from the nozzle arrangement in accordance with the embodiment of the present invention shown in FIGS. 3B-E. The shaded portion represents the area having improved spray coverage. The dotted lines represent individual spray patterns associated with the helical nozzles 308*a-h*. As can be seen, the fan spray patterns associated with the helical nozzles 308 begin with an upper-most nozzle 308*a* having a spray pattern that is oriented approximately at 0 degree roll angle. The spray patterns become progressively steeper, ending with the spray pattern associated with the nozzle 308*h* closest to the closed end 228 of the cylinder 108, which is oriented at approximately a 90 degree roll angle. It has been found that this arrangement of nozzles when combined with the cylinder's rotation provides an advantageous coverage of cleaning spray to the hands and forearms of the user.

It should be understood that the flat fan spray pattern, discussed above in connection with the various nozzles, is presented by way of illustration and not limitation. Alternative embodiments of the present invention may employ nozzles having different spray patterns. For example, the present invention may use nozzles having a spherical spray pattern or a conical spray pattern. Additionally, the present invention may use nozzles that having a pulsing spray or nozzles that have a jetted spray.

Moreover, it should be understood that the nozzles angles discussed above are presented by way of illustration and not limitation. Alternative values for both the pitch and roll angles are considered within the scope of the invention. A particular embodiment of the present invention includes a first nozzle 308*a* disposed at a roll angle of between 0 and 15 degrees, a second nozzle 308*b* disposed at a roll angle of between 15 and 30 degrees, a third nozzle 308*c* disposed at a roll angle of between 30 and 45 degrees, a fourth nozzle 308*d* disposed at a fourth roll angle of between 45 and 60 degrees, a fifth nozzle 308*e* disposed at a roll angle of between 60 and 75 degrees, and a sixth nozzle 308*f* disposed at a roll angle of between 75 and 90 degrees. Another embodiment of the present invention includes a first nozzle 308*a* disposed at a roll angle of between 0 and 11 degrees, a second nozzle 308*b* disposed at a roll angle of between 11 and 22 degrees, a third nozzle 308*c* disposed at a roll angle of between 22 and 33 degrees, a fourth nozzle 308*d* disposed at a fourth roll angle of between 33 and 44 degrees, a fifth nozzle 308*e* disposed at a roll angle of between 44 and 55 degrees, a sixth nozzle 308*f* disposed at a roll angle of between 55 and 66 degrees, a seventh nozzle 308*g* disposed at a roll angle of between 66 and 77 degrees, and an eighth nozzle 308*h* disposed at a eighth roll angle of between 77 and 90 degrees.

Figure 16B:
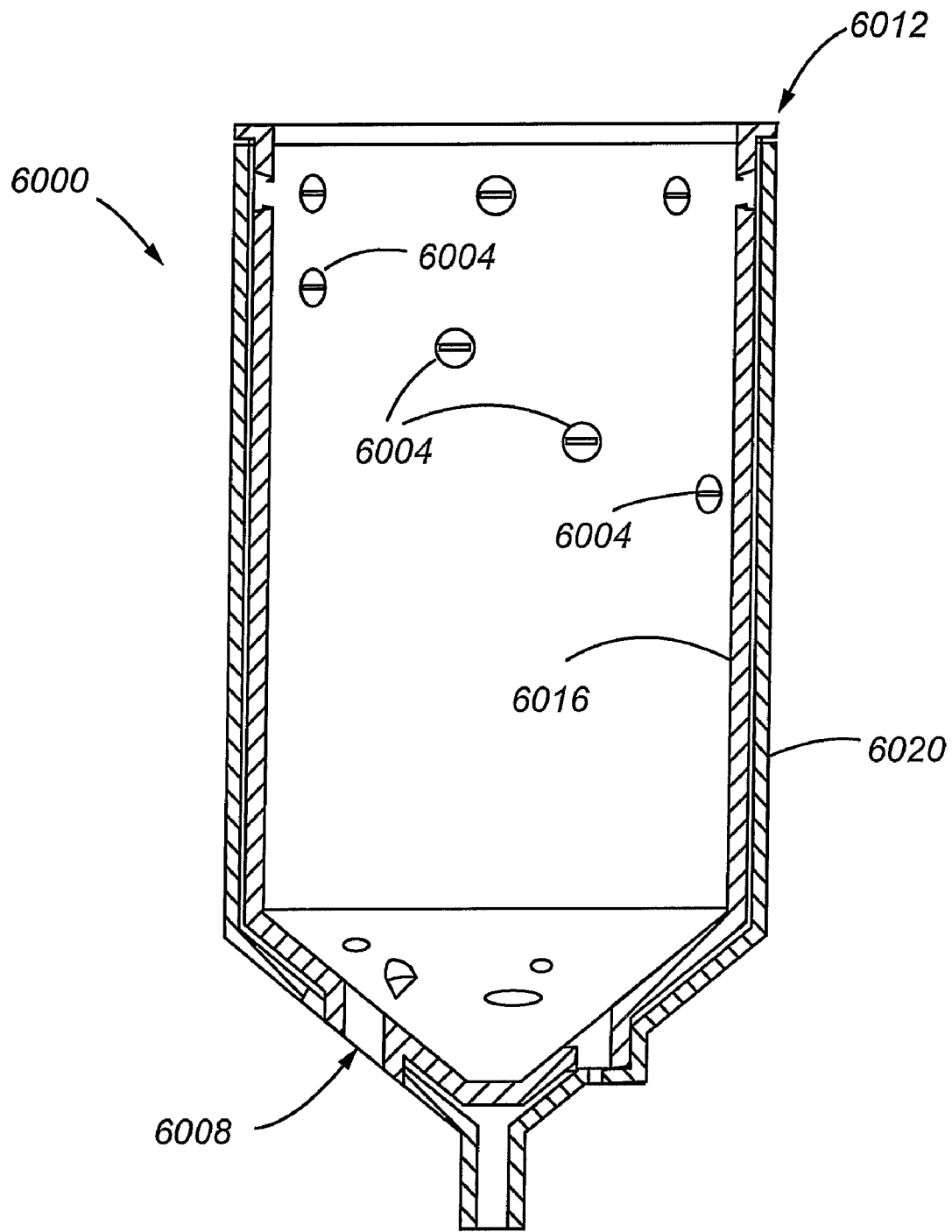
FIG. 16B is a cross-sectional view of a prior art wash cylinder.

The nozzle configurations of the present invention described above differ from nozzle configuration of the prior art in important respects. A configuration of nozzles known in the prior art is shown in FIG. 16B. FIG. 16B includes a wash chamber 6000 having a plurality of helical nozzles 6004. As can be seen, each helical nozzle is oriented to produce a spray pattern having a substantially 90 degree roll angle. Other known prior art nozzle configurations include a first portion of the helical nozzles 6004 which are oriented to produce a spray pattern having a substantially 0 degree roll angle and a second portion of the helical nozzles 6004 which are oriented to produce a spray pattern having a spray pattern having a substantially 90 degree roll. In contrast to the prior art, the present invention includes a nozzle arrangement having helical nozzles 308 oriented at progressively steeper roll angles. Additionally, the present invention may include a number of off-helix nozzles 312.

The wash chamber 6000 shown in FIG. 16B additionally includes other features known in the prior art. In particular, the wash chamber 6000 includes a drain 6008. The drain 6008 has a larger area opening than the drain 236 of the present invention. In contrast to the prior art, the drain 236 of the present invention includes drain holes sized to prevent fingers and/or jewelry from being caught while the cylinder is in motion. Additionally, FIG. 16B shows a top or opening portion 6012 of the wash chamber 6000. In contrast to the present invention, the opening portion 6012 does not include a recessed portion adapted to operate with a circular flange to provide a finger guard. Additionally, the opening portion does not include a flange and lip structure, adapted to provide a water tight seal between the inner cylinder 6016 and the outer cylinder 6020.

Figure 17:
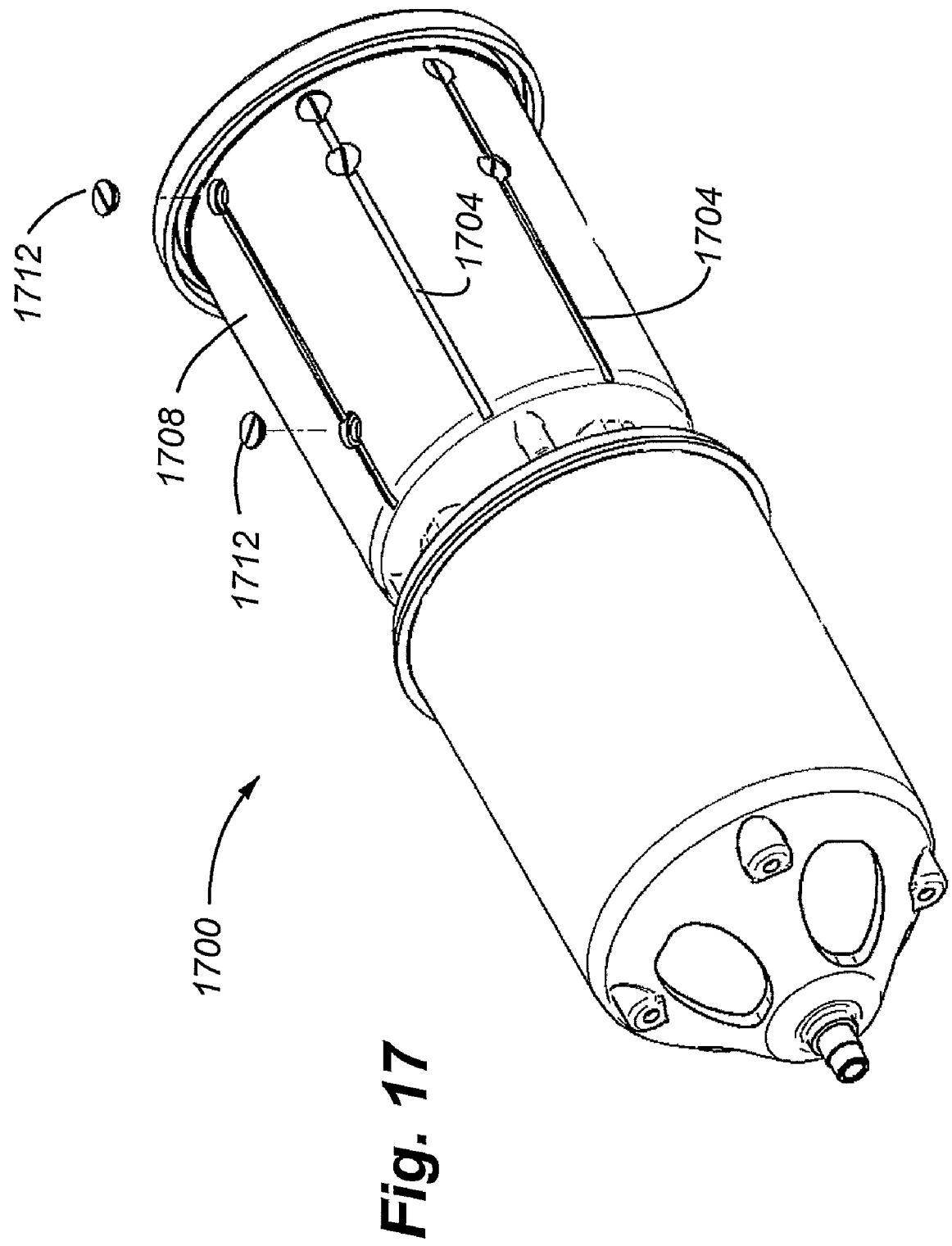
FIG. 17 is a exploded perspective view of an embodiment of the present invention having a fluid conveyance structure.

In accordance with embodiments of the preset invention, the wash cylinder may include a structure for delivering fluid directly to one or more nozzles. The embodiment of the present invention depicted in FIG. 17 includes a wash cylinder 1700 having a plurality of channels 1704 disposed on the inner cylinder 1708. Each channel 1704 serves to direct fluid to one or more nozzles 1712. By delivering fluid directly to the nozzles 1712 the speed at which fluid is delivered to the hand and/or forearm of the user may be increased and the time between wash cycles may be decreased. Furthermore, the volume of fluids used per wash cycle is significantly reduced.

Embodiments of the present invention may include a fluid delivery structure that obviates the need for an outer cylinder. The embodiment of the present invention depicted in FIGS. 18A-B includes a wash cylinder 1800 having a plurality of tubes 1804 associated with a fluid manifold 1808. Initially, fluid enters the fluid manifold 1808 and is then distributed through the tubes 1804 to a plurality of nozzles 1812. Each tube 1804 may deliver fluid from the fluid manifold 1808 to one or more nozzles 1812. By way of illustration and not limitation, each tube 1804 shown in FIGS. 18A-B delivers fluid to one nozzle 1812.

The embodiment of the present invention shown in FIGS. 19A-B includes wash cylinder 1900 having a fluid duct 1904 that delivers fluid from a fluid manifold 1908 to a plurality of nozzles. Initially, fluid enters the fluid manifold 1908 and is distributed through the duct 1904 to the nozzles. As shown in FIGS. 19A-B, the fluid duct 1904 may include a helical portion 1912 having a helical shape, which is adapted to deliver fluid to a series of nozzles arranged in a helical pattern. Additionally, the fluid duct 1904 may include a circular portion 1916 having a circular or partial shape, which is adapted to deliver fluid to a plurality of nozzles arranged in a ring. The helical portion 1912 and the circular portion 1916 may be interconnected, as shown in FIGS. 19A-B. Alternatively, the circular portion 1916 may include a separate fluid delivery structure adapted to deliver fluid from the fluid manifold 1908 to the circular portion 1916.

Both the tube system shown in FIGS. 18A-B and the duct system shown in FIGS. 19A-B, provide an alternative to the wash cylinder 108 having an inner cylinder 316 and an outer cylinder 320. More particularly, the embodiments shown in FIGS. 18A-B and FIGS. 19A-B do not include an annular cavity 324 that is filled and pressurized in order to deliver fluid to a plurality of nozzles. In that regard, the embodiments of the present invention shown in FIGS. 18A-B and FIGS. 19A-B, include one or more void spaces 1816, 1920. The void spaces 1816, 1920 are adjacent to a fluid conveyance structure, such as the plurality of tubes 1804 or the fluid ducts 1904, and are not filled with fluid during the operation of the wash cylinder 1800, 1900. Accordingly, a smaller space is filled each time a particular wash cycle is performed. As a result, the speed at which fluid is delivered to the hand and/or forearm of the user may be increased and the time between wash cycles may be decreased, and the volume of fluid used may be reduced.

Referring now to FIG. 20, and in accordance with at least one embodiment of the present invention, there is shown a single cylinder or wash chamber 2000 with fluid conveyance structure or fluid duct 2004. The fluid duct 2004 conveys fluid to the nozzle 2008. The nozzle 2008 preferably includes an outlet side 2006 that is flush with the inner surface 2010 of the wash chamber 2000, and the nozzle 2008 projects fluid into the appendage receiving cavity 2014 of the wash chamber 2000.

The fluid duct 2004 shown in FIG. 20 resides on an exterior surface 2012 of the wash chamber 2000. The fluid duct 2004 is located a radial distance 2016 from the center 2020 of the wash chamber 2000. A void space 2024 resides adjacent the fluid duct 2004. For the embodiment shown in FIG. 20, the void space 2024 is located a radial distance 2028 from the center 2020 of the wash chamber 2000, wherein the radial distance 2028 of the void space 2024 is substantially equal to the radial distance 2016 from the center 2020 of the wash chamber 2000 to the fluid duct 2004. For the embodiment of the wash chamber 2000 shown in FIG. 20, the void space 2024 is laterally adjacent to the fluid duct 2004 along a circular arc portion. That is, the void space 2024 and the fluid duct 2004 are laterally adjacent while being disposed at substantially the same radial distance from the center 2020. More particularly, the void space 2024 and the fluid duct 2004 are offset from each other by an angle, such as angle Δ shown in FIG. 20.

Still referring to FIG. 20, a second fluid duct 2032 is shown. The second fluid duct 2032 of FIG. 20 comprises a tube. The second fluid duct 2032 may be in fluidic communication with fluid duct 2004, or it may not be in fluidic communication with the fluid duct 2004.

Referring now to FIG. 21, and in accordance with at least one embodiment of the present invention, there is shown a wash chamber 2100 comprising an outer member 2104 and an inner member 2108. An annular cavity 2112 is located between the outer member 2104 and the inner member 2108, and at least one fluid conveyance structure or fluid duct 2116 directs fluid to a nozzle 2120. For the embodiment shown in FIG. 21, the fluid duct 2116 comprises a tube. The nozzle 2120 preferably includes an outlet side 2124 that is flush with the inner surface 2128 of the inner member 2108, and the nozzle 2120 projects fluid into the appendage receiving cavity 2132 of the wash chamber 2100.

The fluid duct 2116 is located a radial distance 2136 from the center 2140 of the wash chamber 2100. A void space 2144 resides within the annular cavity 2112 and adjacent the fluid duct 2116. For the embodiment shown in FIG. 21, the void space 2144 is located a radial distance 2148 from the center 2140 of the wash chamber 2100, wherein the radial distance 2148 of the void space 2144 is substantially equal to the radial distance 2136 from the center 2140 of the wash chamber 2100 to the fluid duct 2116. For the embodiment of the wash chamber 2100 shown in FIG. 21, the void space 2144 is located along a different alignment or angular vector than the fluid duct 2116 relative to the center 2140 of the wash chamber 2100. That is, the void space 2144 is laterally adjacent the fluid duct 2116, but the void space 2144 is offset at an angle relative to the center 2140, such as angle Δ shown in FIG. 21.

Still referring to FIG. 21, additional fluid ducts 2152 are shown. The additional fluid ducts 2152 of FIG. 21 comprise tubes. For the embodiment shown in FIG. 21, the additional fluid ducts 2152 are not in fluidic communication with fluid duct 2116, although they may be in fluidic communication with the fluid duct 2116, such as by way of a laterally oriented tube (not shown).

Although the wash chambers described herein are anticipated for use in cleaning stations, the chambers may be used in non-cleaning uses or uses where cleaning the appendage is not the principal purpose of use (although some cleaning may still occur), such as for application of a topical treatment to an appendage. By way of example and not limitation, the appendage receiving members, chambers, and/or cylinders described herein may be used within an alternate device such as a solution dispensing apparatus for application or treating an appendage with a liquid, such as a liquid containing a medicinal agent or compound. Alternate uses include a system for application of: a tanning agent to an appendage; a moisturizer or non-medical treatment (e.g., perfume, deodorant, etc.) to an appendage; a chemical depilatory to remove hair from an appendage; a hot wax to an appendage; etc.

Embodiments of the present invention may also be used for applying a liquid to a tangible object or other item other than an person's appendage. For example, the automated cleaning stations or adaptations thereof can be used to wash, rinse, and/or apply a liquid to an animal or an object, such as an object that is being held by a person's hand, or that is being held by a holding mechanism, such as a support or a clamp. Such automated cleaning stations, sub-assemblies, components and/or adaptations thereof are within the scope of the present invention.

The following U.S. Patents are incorporated herein by reference in their entirety: U.S. Pat. Nos. 5,823,447, 5,265,628; 4,817,651; and 4,925,495.

The present invention, in various embodiments, includes components, methods, processes, systems and/or apparatus substantially as depicted and described herein, including various embodiments, subcombinations, and subsets thereof. Those of skill in the art will understand how to make and use the present invention after understanding the present disclosure. The present invention, in various embodiments, includes providing devices and processes in the absence of items not depicted and/or described herein or in various embodiments hereof, including in the absence of such items as may have been used in previous devices or processes, e.g., for improving performance, achieving ease and/or reducing cost of implementation.

It is to be noted that the term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The foregoing discussion of the invention has been presented for purposes of illustration and description. The foregoing is not intended to limit the invention to the form or forms disclosed herein. In the foregoing Detailed Description for example, various features of the invention are grouped together in one or more embodiments for the purpose of streamlining the disclosure. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the invention.

Moreover, though the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method, comprising:
   initiating a flow of a first fluid into a rotatable wash chamber of a cleaning station, the rotatable wash chamber including a first end and a second end, at least one of the first end and the second end connected to the cleaning station, the wash chamber including an axis of rotation, the wash chamber including an appendage receiving cavity located within and defined by the wash chamber, the appendage receiving cavity being accessible through an opening in the first end of the wash chamber and being adapted to receive at least a portion of the appendage for washing, wherein the wash chamber comprises a housing enclosing substantially the appendage receiving cavity, the appendage receiving cavity being accessible by the at least one appendage through an opening in the housing;

rotating the wash chamber;

conveying the first fluid directly to at least one nozzle of a plurality of nozzles disposed on the housing, the conveying including routing the first fluid through a fluid conveyance structure that delivers the first fluid to the at least one nozzle, the fluid conveyance structure located adjacent to a void space, wherein the fluid conveyance structure is offset from a center of the wash chamber at least a first radial distance, the center being substantially collocated along the axis of rotation of the wash chamber, wherein the void space is located at a second radial distance from the center of the wash chamber, wherein the first radial distance is substantially equal to the second radial distance for a given longitudinal position along a longitudinal length of the wash chamber, and wherein, when the fluid conveyance structure is filled with the first fluid, the void space is not filled with the first fluid; and projecting the first fluid through a fluid inlet, through the fluid conveyance structure, and the at least one nozzle, and into the appendage receiving cavity;

wherein the wash chamber is rotated about the axis of rotation at least during the step of projecting the fluid.

2. The method of claim 1, wherein the fluid conveyance structure includes a tube extending from a fluid manifold proximate to the fluid inlet to the at least one nozzle of the plurality of nozzles and wherein the wash chamber is free of an outer housing.

3. The method of claim 1, wherein the fluid conveyance structure conveys the first fluid to a subset of the plurality of nozzles, the subset including the at least one nozzle but not all of the plurality of nozzles, wherein the fluid conveyance structure is a tube, wherein each of a plurality of tubes services a multi-member set of nozzles, and wherein the plurality of tubes are in fluid communication with a common manifold.

4. The method of claim 1, wherein the void space is spaced apart from the fluid conveyance structure along an arc length of the wash chamber, wherein the fluid conveyance structure comprises the first fluid, and wherein, at the same time, the void space is free of the first fluid.

5. The method of claim 1, wherein the wash chamber further comprises an inner member, an outer member, and an annular cavity located between the inner member and the outer member, wherein the fluid conveyance structure and the void space are located between the inner member and the outer member.

6. The method of claim 1, wherein the fluid conveyance structure comprises one or more of a tube, duct, channel and groove, wherein the housing comprises inner and outer cylinders, and wherein an annular space between the inner and outer cylinders is divided into one or more fluid conveyance structures and one or more void spaces.

7. The method of claim 1, wherein the fluid conveyance structure includes a first fluid duct extending from a fluid manifold proximate to the fluid inlet at an end of the wash chamber, to the at least one nozzle of the plurality of nozzles, wherein the housing comprises inner and outer cylinders, and wherein an annular space between the inner and outer cylinders is divided into one or more fluid conveyance structures and one or more void spaces.

8. The method of claim 7, wherein the housing comprises inner and outer cylinders, wherein an annular space between the inner and outer cylinders is divided into one or more fluid conveyance structures and one or more void spaces, and wherein the plurality of nozzles includes:

a first set of nozzles disposed on cylindrical portion of the wash chamber in a helical pattern;

wherein the first fluid duct connects each nozzle in the first set of nozzles to the fluid manifold.

9. The method of claim 8, wherein the fluid conveyance structure includes a second fluid duct and the plurality of nozzles includes a second set of nozzles disposed on the wash chamber in a ring proximate to the first end of the wash chamber, wherein the second fluid duct connects each nozzle in the second set of nozzles to the fluid manifold.

10. The method of claim 9, where the first fluid duct and the second fluid duct are interconnected.

11. The method of claim 1, wherein the fluid conveyance structure delivers the first fluid to a discrete subset of the plurality of nozzles, the discrete subset comprising the at least one nozzle and at least a second nozzle of the plurality of nozzles, and wherein the void space is not enclosed fully by the housing.

12. A method, comprising:

providing a cleaning station, comprising a rotatable wash chamber;

an appendage receiving cavity located within and enclosed substantially by a housing member, the appendage receiving cavity being accessible, by at least a portion of an appendage of a user, through an opening in the wash chamber;

a plurality of nozzles disposed on the wash chamber; and at least one fluid conveyance structure positioned in the annular space and in communication with at least one nozzle, the at least one fluid conveyance structure dividing the annular space into fluid carrying and non-fluid carrying portions, whereby, when the fluid carrying portion comprises the at least one cleaning fluid, the non-fluid carrying portion is free of the at least one cleaning fluid;

rotating the rotatable wash chamber;

conveying at least one cleaning fluid to at least one nozzle of the plurality of nozzles, the conveying including routing the at least one cleaning fluid through the fluid conveyance structure that delivers the at least one cleaning fluid to the at least one nozzle; and projecting the at least one cleaning fluid through the plurality of nozzles and into the appendage receiving cavity.

13. The method of claim 12, wherein the fluid conveyance structure conveys the at least one cleaning fluid to a subset of the plurality of nozzles, the subset including the at least one nozzle but not all of the plurality of nozzles, wherein the fluid conveyance structure is a tube, wherein each of a plurality of tubes services a multi-member set of nozzles, and wherein the plurality of tubes are in communication with a common manifold.

14. The method of claim 12, wherein the at least one fluid conveyance structure comprises a plurality of fluid conveyance structures and wherein the fluid conveyance structures are in communication with a common manifold.

15. The method of claim 14, wherein the manifold comprises an fluid input and a protrusion positioned on a surface opposite the fluid input to redirect the at least one cleaning fluid flowing through the fluid input, and wherein the protrusion is sloped.

16. The method of claim 12, wherein at least first and second nozzles of the plurality of nozzles are mounted on a common inlay, the inlay being removably disposed on the wash chamber, and wherein the first and second nozzles receive the at least one fluid from a common fluid conveyance structure.

17. The method of claim 12, wherein the housing member comprises inner and outer cylinders, wherein an annular space between the inner and outer cylinders is divided into one or more fluid conveyance structures and one or more void spaces, and wherein the one or more fluid guidance structures comprises one or more of a tube, duct, channel, and groove.

18. A method, comprising:
   providing a cleaning station, comprising:
   a rotatable wash chamber, the wash chamber comprising a housing;
   an appendage receiving cavity located within and substantially enclosed by the housing, the appendage receiving cavity being accessible, by at least a portion of an appendage of a user, through an opening in the housing;
   a plurality of nozzles disposed on the housing; and
   a plurality of fluid conveyance structures positioned at discrete intervals on an exterior of the housing and in communication with the plurality of nozzles, wherein a substantial portion of the housing exterior is free of fluid conveyance structures;
   conveying at least one cleaning fluid to the plurality of nozzles, the conveying including routing the at least one cleaning fluid through the plurality of fluid conveyance structures that delivers the at least one cleaning fluid to the plurality of nozzles; and
   projecting the at least one cleaning fluid through the plurality of nozzles and into the appendage receiving cavity.

19. The method of claim 18, wherein the plurality of fluid conveyance structures are in fluid communication with a common manifold.

20. The method of claim 18, wherein a plurality of the nozzles provide spray patterns that differ in at least one of a roll angle and a pitch angle.

* * * * *